United States Patent
Safdar et al.

(10) Patent No.: US 8,180,126 B2
(45) Date of Patent: May 15, 2012

(54) DETECTING MENISCAL TEARS IN NON-INVASIVE SCANS

(75) Inventors: Nabile Safdar, Elkridge, MD (US); Bharath Ramakrishna, Bangalore (IN); Chein-I Chang, Ellicott City, MD (US); Wei-min Liu, Taipei (TW); Khan Siddiqui, Highland, MD (US); Eliot Siegel, Saverna Park, MD (US)

(73) Assignees: University of Maryland, Baltimore, Baltimore, MD (US); University of Maryland, Baltimore County, Baltimore, MD (US)

( * ) Notice: Subject to any disclaimer, the term of this patent is extended or adjusted under 35 U.S.C. 154(b) by 923 days.

(21) Appl. No.: 12/190,584

(22) Filed: Aug. 12, 2008

(65) Prior Publication Data
US 2009/0046908 A1 Feb. 19, 2009

Related U.S. Application Data

(60) Provisional application No. 60/964,461, filed on Aug. 13, 2007.

(51) Int. Cl.
*G06K 9/00* (2006.01)
(52) U.S. Cl. .................................................. 382/128
(58) Field of Classification Search .................. 382/128
See application file for complete search history.

(56) References Cited

U.S. PATENT DOCUMENTS

| | | | |
|---|---|---|---|
| 7,555,153 B2 * | 6/2009 | Martel-Pelletier et al. | 382/131 |
| 2005/0148858 A1 * | 7/2005 | Hargreaves | 600/410 |
| 2006/0239523 A1 * | 10/2006 | Stewart et al. | 382/128 |
| 2010/0220907 A1 * | 9/2010 | Dam et al. | 382/131 |

OTHER PUBLICATIONS

Hata, Y., Kobashi, S., Tokimoto, Y., Ishikawa, M., and Ishikawa, H., Computer Aided Diagnosis System of Meniscal Tears with T1 and T2 Weighted MR Images Based on Fuzzy Inference, Fuzzy Days 2001, 2001, pp. 55-58, vol. LNCS 2206, Publisher: Springer-Verlag, Published in: Berlin.

* cited by examiner

*Primary Examiner* — W. B. Perkey
(74) *Attorney, Agent, or Firm* — Evans & Molinelli PLLC; Eugene J. Molinelli

(57) ABSTRACT

Techniques for automatically detecting meniscus include receiving pixels from a scanning device directed to a knee of a subject. Also received is a region of interest that includes pixels that correspond to at least a portion of a meniscus of the knee. Without human intervention, a meniscus extraction threshold is determined based on pixel intensities in the region of interest. A meniscus object portion of the scan data is further determined without human intervention based on the meniscus extraction threshold and a geometrical constraint. Other techniques for automatically detecting meniscal tears includes receiving a meniscus object portion of scan data from a scanning device and receiving threshold data that indicates a meniscus extraction threshold. Without human intervention, a propensity for meniscal tears is determined based on the threshold data and the meniscus object portion of the scan data.

10 Claims, 16 Drawing Sheets

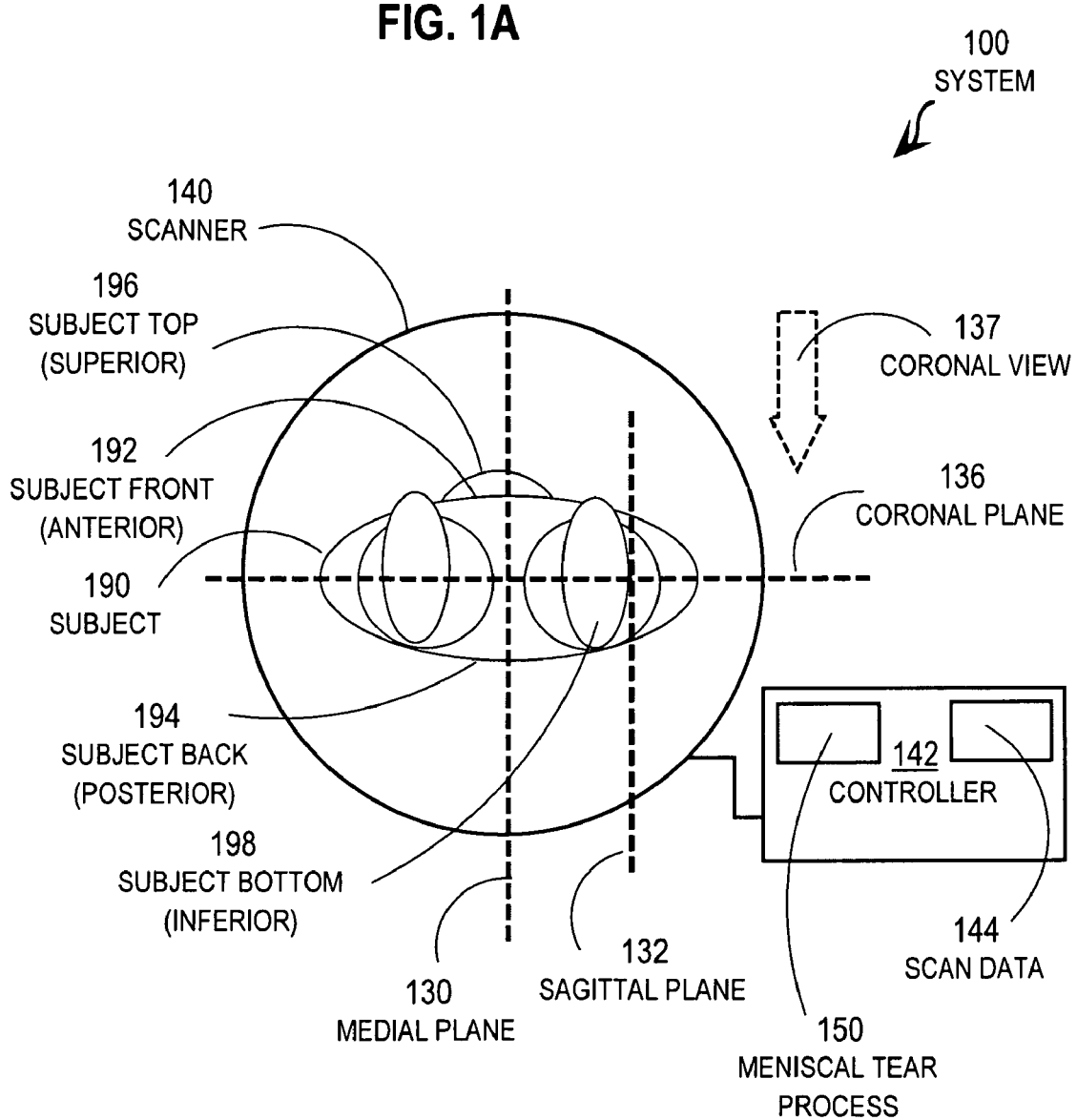

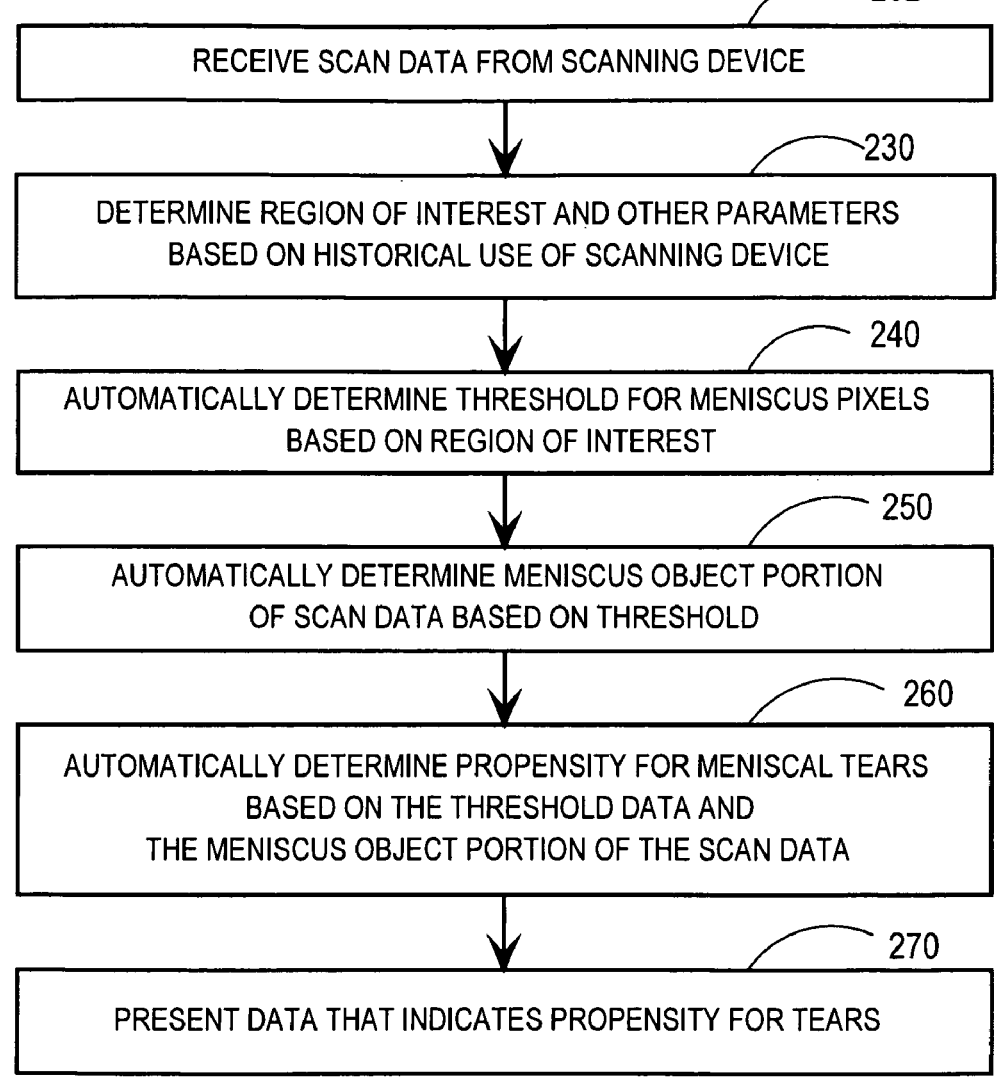

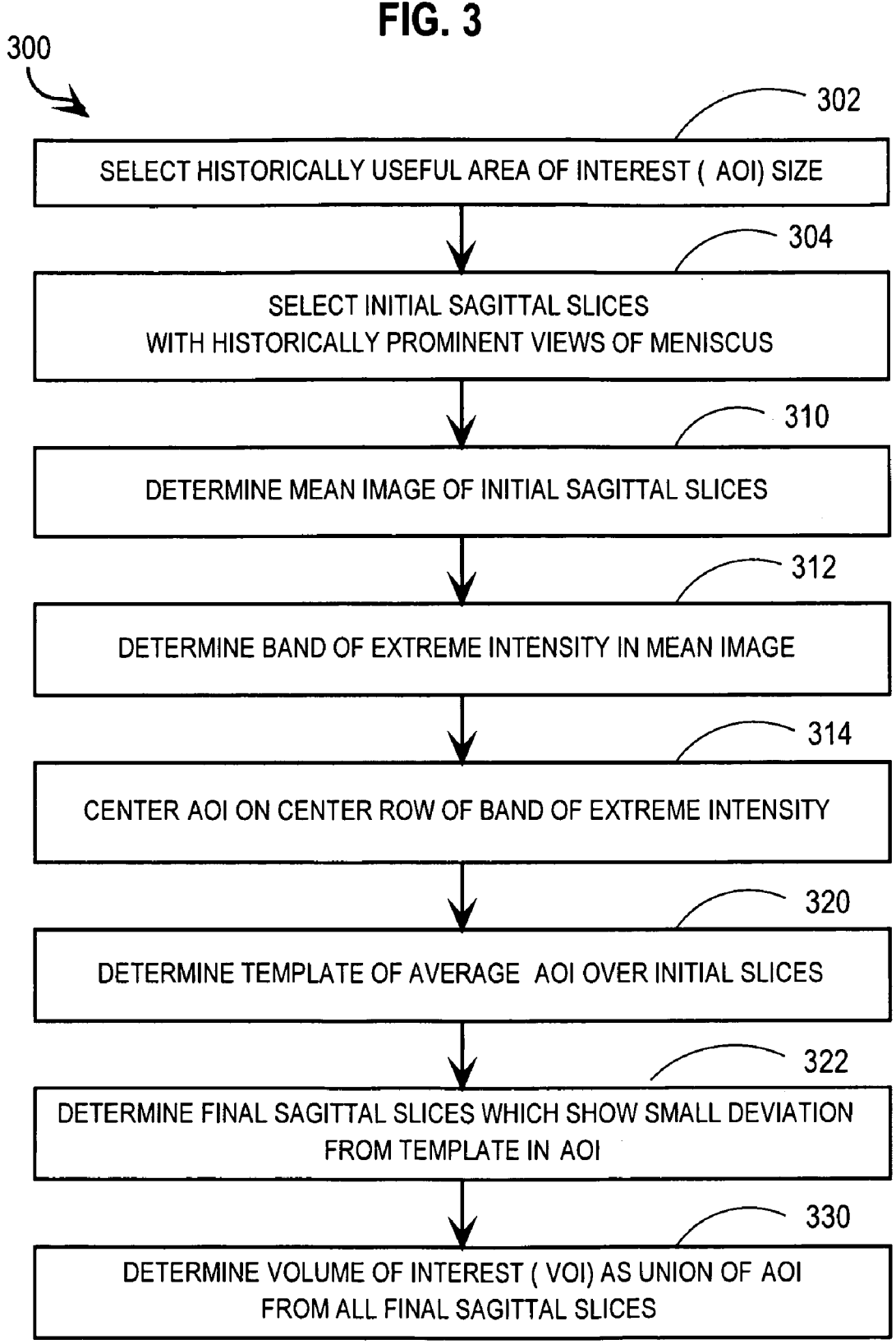

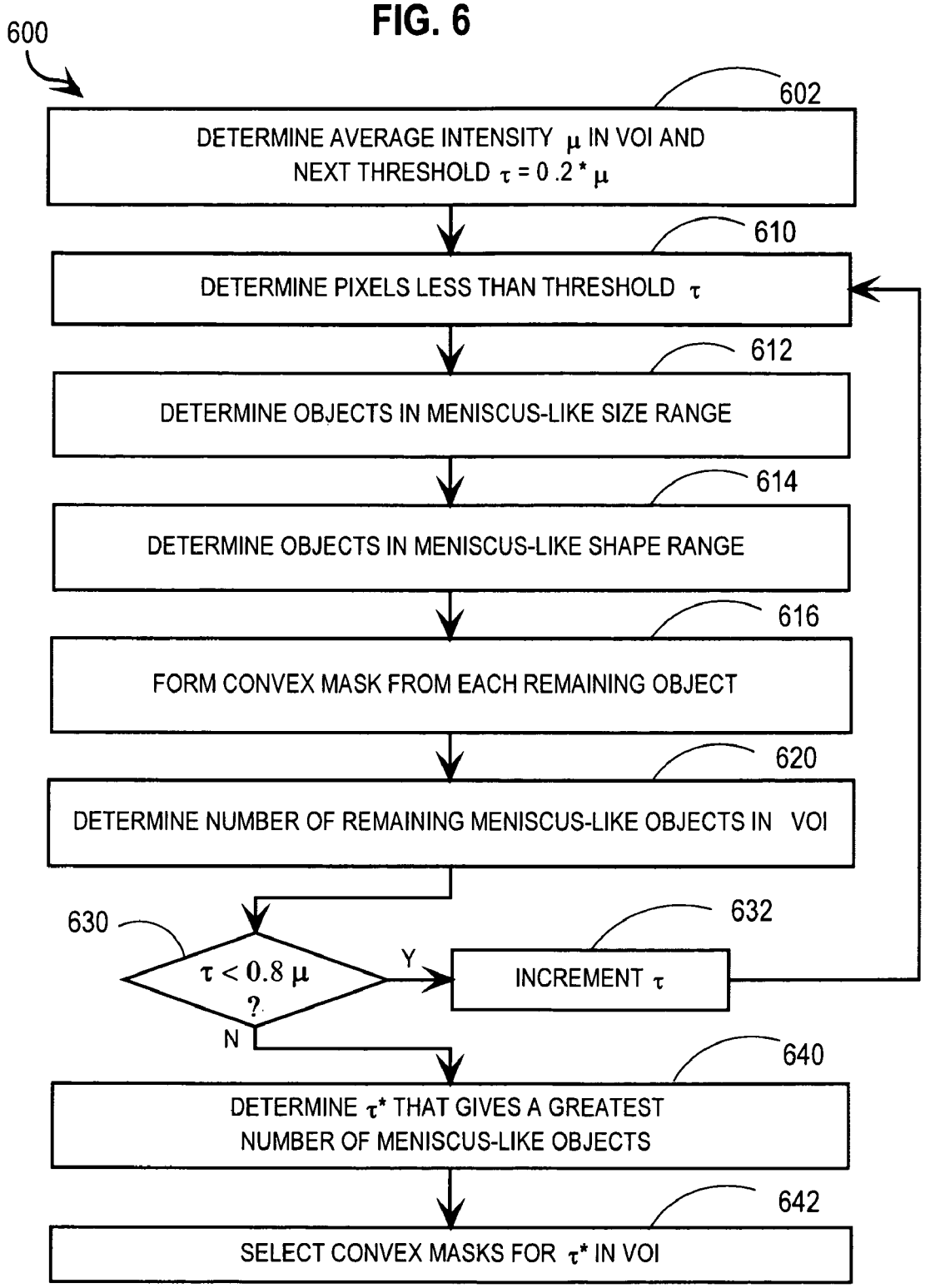

710 OBJECT (CONNECTED PIXELS BELOW THRESHOLD)

720 OBJECT BOUNDING BOX
724 MINOR AXIS
722 MAJOR AXIS

730 CONVEX MASK
734 MINOR AXIS
732 MAJOR AXIS

740 MASK WITH CARTILAGE REMOVED
742 PIXELS ABOVE 0.8 μ

810 SAGITTAL SLICE IN FINAL SET

812 AOI IN SLICE

812 AOI IN SLICE

820 BINARY IMAGE AT PARTICULAR THRESHOLD

830
AOI BINARY IMAGE
OF OBJECTS IN SIZE RANGE

840a
BONDING BOX BINARY IMAGE OF
FIRST OBJECT IN SHAPE RANGE

840b
BONDING BOX BINARY IMAGE OF
SECOND OBJECT IN SHAPE RANGE

850a
BONDING BOX CONVEX MASK OF
FIRST OBJECT

850b
BONDING BOX CONVEX MASK OF
SECOND OBJECT

860a
INTENSITY IMAGE IN
CONVEX MASK OF FIRST OBJECT

860b
INTENSITY IMAGE IN
CONVEX MASK OF SECOND OBJECT

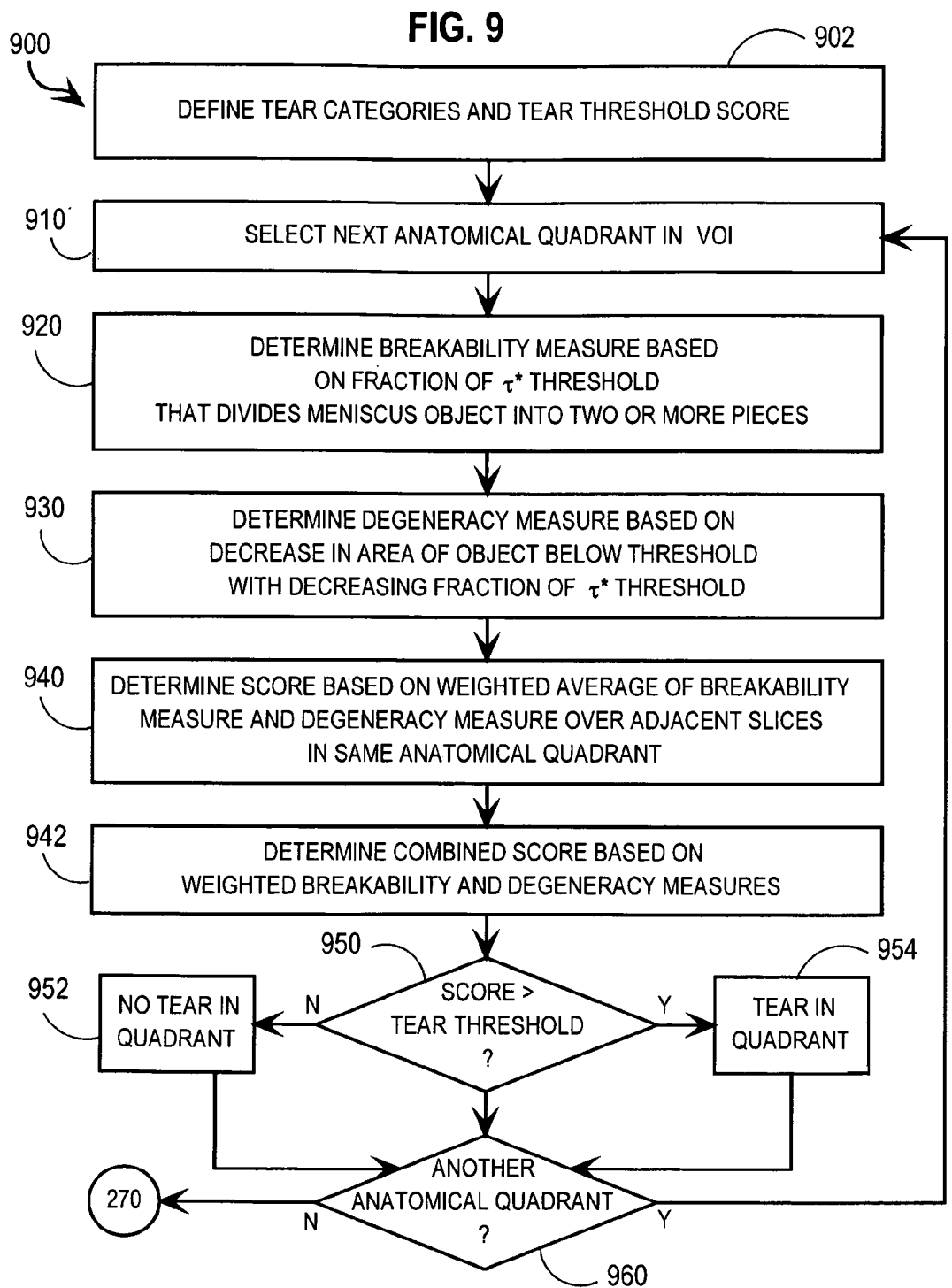

DETECTING MENISCAL TEARS IN NON-INVASIVE SCANS

CROSS-REFERENCE TO RELATED APPLICATIONS

This application claims benefit of Provisional Appln. 60/964,461, filed Aug. 13, 2007, the entire contents of which are hereby incorporated by reference as if fully set forth herein, under 35 U.S.C. §119(e).

STATEMENT OF GOVERNMENTAL INTEREST

This invention was made in part with US Government support from the Department of Veterans Affairs (VA). The Government has certain rights in the invention.

BACKGROUND OF THE INVENTION

1. Field of the Invention

The present invention relates to interpreting non-invasive scans of a knee of a subject to determine properties of a meniscus of the knee, and, in particular, to determining one or more properties of the meniscus, such as tears, without human intervention.

2. Description of the Related Art

The meniscus is an important part of the knee support mechanism. It includes 2 large C-shaped (medial side) and O-shaped (lateral side) structures and acts as a cushion between the femur and the tibia. Although the meniscus is highly tolerant to axial forces, it is susceptible to rotational forces, which may result in meniscal tearing. If a tear originating in the periphery of the meniscus is left untreated, it propagates easily and may affect the mechanical integrity of the entire knee joint. Knee-related injuries, including meniscal tears, are common in both young athletes and the aging population, requiring accurate diagnosis and, when appropriate, surgical intervention. Despite the frequency of such injuries, few published studies have focused on means to enhance and refine detection of meniscal tears. (See for example, Y Hata, S Kobashi, S Tokimoto, M Ishikawa, H Ishikawa, "Computer-aided diagnosis system of meniscal tears with T1- and T2-weighted MR images based on fuzzy inference," Lect Notes *Comput Sci*, vol. 2206, pp 55-58, 2001).

The meniscus is a soft tissue feature with low contrast in imagery from many scanning devices, such as X-rays and X-ray computer tomography (CT) scans. The superior soft-tissue contrast and spatial resolution provided by magnetic resonance (MR) imaging enables radiologists to characterize and differentiate pathologic from normal soft tissue, including meniscus tissue. MR imaging offers significant and specific help in the diagnosis of internal derangements of the knee, including meniscal tears. A normal meniscus appears as uniform, low-signal triangles or polygons on certain slices of MR imaging. However, when the meniscus is torn, the normal low-signal appearance is disrupted. A meniscal tear, then, can be detected if the normal shape of the meniscus is disrupted by an abnormal signal or if part of the meniscus is missing. Challenges in diagnoses of meniscal pathology include differentiation of tears, which indicate a need for surgery, from internal degenerative change, which would obviate the need for surgery.

With proper techniques and experienced skills, confidence in detection of meniscal tears by a skilled radiologist can be quite high. However, for radiologists without musculoskeletal training, diagnosis of meniscal tears can be challenging. Even for highly experienced radiologists, the effort to explore multiple images from the MR scans and identify views of the meniscus with sufficient area and detail to detect tears is tedious and time consuming and can lead to errors of omission if a salient scan slice is skipped.

SUMMARY OF THE INVENTION

In a first set of embodiments, a method for automatically detecting meniscus in non-invasive scans includes receiving scan data from a scanning device, in which the scan data is directed to a knee of a subject. Data that indicates a region of interest within the scan data is also received. The region of interest includes scan elements that correspond to at least a portion of a meniscus of the knee of the subject. Without human intervention, a meniscus extraction threshold is determined based on scan element intensities in the region of interest. A meniscus object portion of the scan data is further determined without human intervention based on the meniscus extraction threshold and a geometrical constraint.

In some of these embodiments, receiving the data that indicates the region of interest includes determining the region of interest within the scan data without human intervention based on historical usage of the scanning device.

In some of the first set of embodiments, determining the meniscus extraction threshold includes determining a single average intensity of all the scan elements in the region of interest, and determining the meniscus extraction threshold as a numeric factor of the average intensity.

In a second set of embodiments, a method for automatically detecting meniscal tears in non-invasive scans includes receiving a meniscus object portion of scan data from a scanning device and receiving threshold data that indicates an intensity threshold used to define the meniscus object portion of the scan data. Without human intervention, a propensity for meniscal tears is determined based on the threshold data and the meniscus object portion of the scan data.

In some of the embodiments of the second set, receiving the meniscus object portion of the scan data includes determining the meniscus object portion from the scan data without human intervention.

In some of the embodiments of the second set, determining the propensity for meniscal tears includes determining a breakability measure based on a largest breaking fraction of a plurality of fractions of the particular intensity used to define the meniscus object portion. A threshold based on a breaking fraction divides the meniscus object portion into multiple distinct portions.

In some of the embodiments of the second set, determining the propensity for meniscal tears includes determining a degeneracy measure. The degeneracy measure is based on decrease in area of the meniscus object portion that is within a threshold, when the threshold is equal to a fraction of the particular intensity used to define the meniscus object portion. The decrease in area is determined for multiple fractions of the particular intensity.

In some of the embodiments of the second set, determining the propensity for meniscal tears includes determining if a property in the meniscus object portion of the scan data is similar to properties in historical scan data for which a tear occurred. If so, then it is determined that the scan data indicates a tear in a meniscus of the knee of the subject.

In various other embodiments, an apparatus, or logic encoded in one or more tangible media, or instructions encoded on one or more computer-readable media is configured to perform one or more steps of the above methods.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1A is a block diagram that illustrates a example imaging system for meniscus tissue, according to an embodiment

FIG. 2 is a flow diagram that illustrates at a high level an example method for automatically detecting meniscus tissue and meniscal tears, according to an embodiment;

FIG. 3 is a flow diagram that illustrates at a high level an example method for automatically determining a region of interest, according to an embodiment;

FIG. 6 is a flow diagram that illustrates at a high level an example method for automatically detecting meniscus tissue, according to an embodiment;

FIG. 9 is a flow diagram that illustrates at a high level an example method for automatically determining a propensity for meniscal tears, according to an embodiment;

DETAILED DESCRIPTION

Figure 1B:
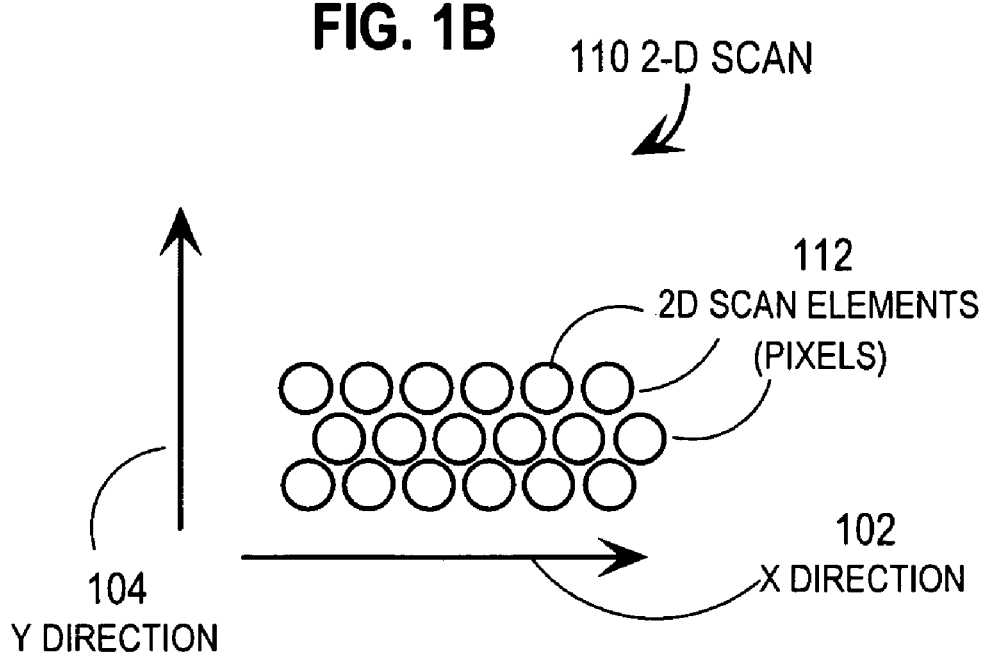
FIG. 1B is a block diagram that illustrates scan elements in a 2D scan.

A method and apparatus are described for detecting meniscus tissue or tears therein, or both. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of current MR imagery used by radiologists to detect meniscal tears. In this kind of imagery, the meniscus tissue is represented by the lowest intensities inside the outer surface of the subject and pixel sizes are about 0.3125 millimeters (mm, 1 mm=$10^{-3}$ meters) across. However, the invention is not limited to this context. In other embodiments, other scanning devices that also differentiate meniscus tissue from cartilage tissue and that also show varying intensity within meniscus tissue, no matter the range of intensities, are used with larger or smaller pixel sizes, including future MR scanners, CT-scanners, multispectral CT scanners, ultrasound scanners, positron emission tomography (PET), and other appropriate medical imagining devices known by one of ordinary skill in the art at the time an embodiment is implemented.

1. Overview

FIG. 1A is a block diagram that illustrates an imaging system 100 for meniscus tissue, according to an embodiment.

The system 100 is designed for determining the spatial arrangement of soft target tissue in a living body. For purposes of illustration a living body is depicted as subject 190, but is not part of the system 100. In the illustrated embodiment, the subject 190 is depicted in a supine position with feet closest to the viewer and pointing up, and head on the far side. The view of FIG. 1A is in a plane perpendicular to a long axis of the subject 190, which is called herein an axial plane. Positions in the subject 190 closer to the subject bottom 198 are said to be inferior; while positions closer to the subject top 196 are said to be superior. Positions in the subject 190 closer to the subject front 192 are said to be anterior; while positions closer to the subject back 194 are said to be posterior. A medial plane, perpendicular to the axial plane, divides the left half of the subject from the right half and is a symmetry axis of approximate reflected symmetry. A coronal plane 136 is perpendicular to both the axial plane and the medial plane 130. A front view direction of the coronal plane is the coronal view direction 137. A sagittal plane 132 is parallel to the medial plane 130. A side of a knee closer to the medial plane is called the medial side, and the opposite side of the knee is the lateral side. The meniscus in each knee of the subject 190 includes a large C-shaped medial meniscus and large O-shaped lateral meniscus.

In the illustrated embodiment, system 100 includes a scanning device, scanner 140, such as a full dose X-ray computed tomography (CT) scanner, a multi-spectral CT scanner, or a magnetic resonance imaging (MRI) scanner. In some embodiments, the scanner 140 is used at two or more different times. The scanner 140 is configured to produce scanned images, such that each image represents a cross section of the living body at one of multiple cross sectional (transverse) slices, often approximately parallel to the axial plane, and often initially arranged along the axial direction of the subject.

In system 100, the scanner is controlled by one or more devices, such as one or more networked computers, represented by controller 142. Data from the scanner 140 is received at a controller 142 and stored on a storage device as scan data 144. Computer systems and storage devices, as in controller 142, are described in more detail in a later section.

In various embodiments, a meniscal tear process 150 operates on controller 142 to determine a boundary between scan elements of scan data which are inside and outside a meniscus and process the scan elements inside the boundary to determine a propensity for tears.

Although system 100 is depicted with a particular number of scanners 140, controllers 142 and scan data 144 for purposes of illustration, in other embodiments more scanners, controllers or scan data constitute an imaging system for determining properties of meniscus tissue.

FIG. 1B is a block diagram that illustrates scan elements in a 2D scan 110, such as one scanned image from a MR scanner. The two dimensions of the scan 110 are represented by the x direction arrow 102 and the y direction arrow 104. The scan 110 consists of a two dimensional array of 2D scan elements often called picture elements (pixels) 112 each with an associated position. Typically, a 2D scan element position is given by a row number for rows oriented in the x direction and a column number for columns oriented in the y direction of a rectangular array of scan elements. A value at each scan element position represents a measured or computed intensity that represents a physical property (e.g., X-ray absorption, or resonance frequency of an MRI scanner) at a corresponding position in at least a portion of the subject 190. Although a particular number and arrangement of equal sized circular scan elements 112 are shown for purposes of illustration, in other embodiments, more elements in the same or different arrangement with the same or different sizes and shapes are included in a 2D scan.

Figure 1C:
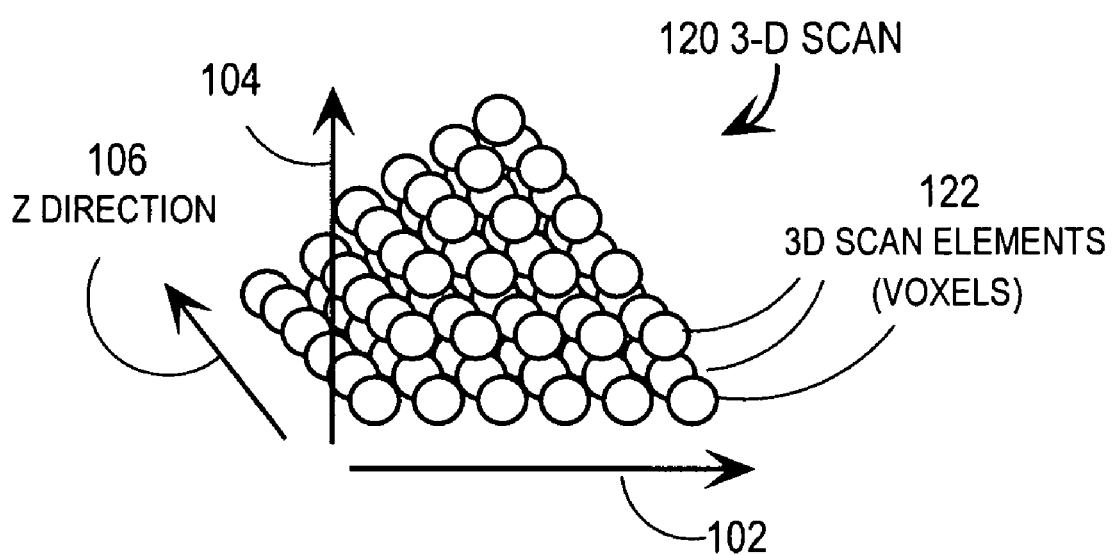
FIG. 1C is a block diagram that illustrates scan elements in a 3D scan.

FIG. 1C is a block diagram that illustrates scan elements in a 3D scan 120, such as stacked multiple scanned images from a 2D MR scanner or true 3D scan elements from volumetric CT imagers and MR scanners. The three dimensions of the scan are represented by the x direction arrow 102, the y direction arrow 104, and the z direction arrow 106. The scan 120 consists of a three dimensional array of 3D scan elements (also called volume elements and abbreviated as voxels) 122 each with an associated position. Typically, a 3D scan element position is given by a row number, column number and a scanned image number (also called a scan number) in the z direction of a cubic or volumetric array of scan elements. A value at each scan element position represents a measured or computed intensity that represents a physical property (e.g., X-ray absorption for a CT scanner, or resonance frequency of an MRI scanner) at a corresponding position in at least a portion of the subject 190. Although a particular number and arrangement of equal sized spherical scan elements 122 are shown for purposes of illustration, in other embodiments, more elements in the same or different arrangement with the same or different sizes and shapes are included in a 3D scan.

The terms scan elements, pixels and voxels are used interchangeably herein to represent either 2D scan elements (pixels) or 3D scan elements (voxels), or both, depending on the context. A 2D image at any orientation (e.g., axial, coronal or sagittal, among others) can be constructed from a 3D array of scan elements by collecting the scan elements closest to a selected plane for the image.

Figure 1D:
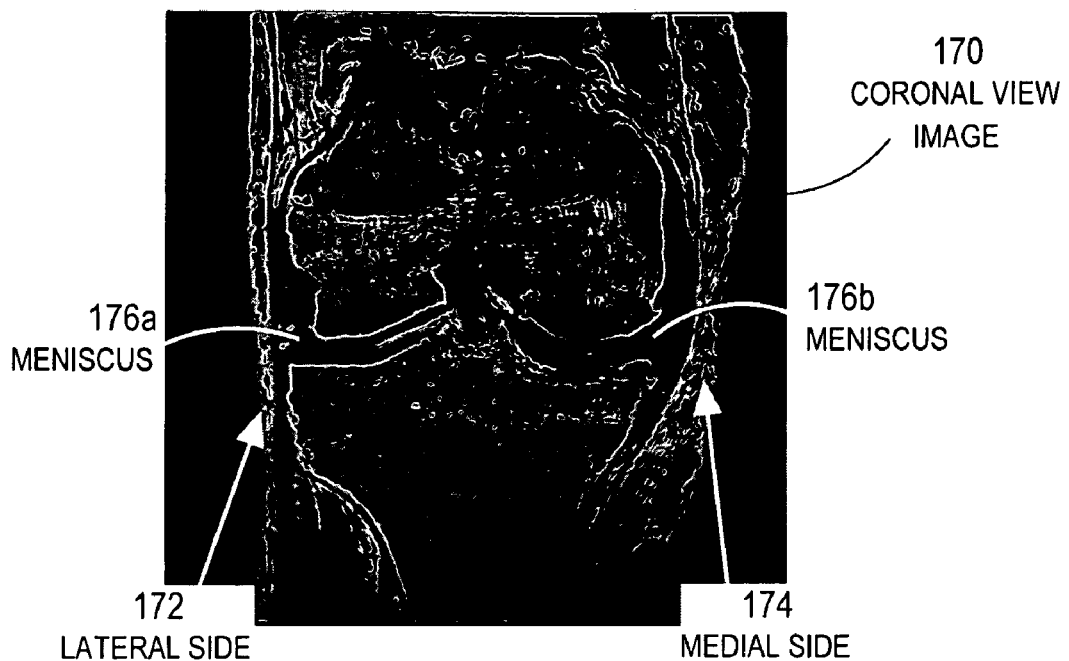
FIG. 1D is an image that illustrates an example coronal view of scan data on one coronal plane.

FIG. 1D is an image that illustrates an example coronal view 170 of scan data on one coronal plane. The superior side of the subject is up, and the medial side 174 of the imaged knee is to the right, while the lateral side 172 is to the left. Varying intensity is indicated by varying shades of gray, with black indicating no intensity. The large light gray areas are bone, including portions of the tibia, below, and femur, above. Small, triangular shaped dark areas of low intensity at a joint between the tibia and femur represent the meniscus in this slice, including portions of the lateral meniscus 176a and the medial meniscus 176b.

Figure 1E:
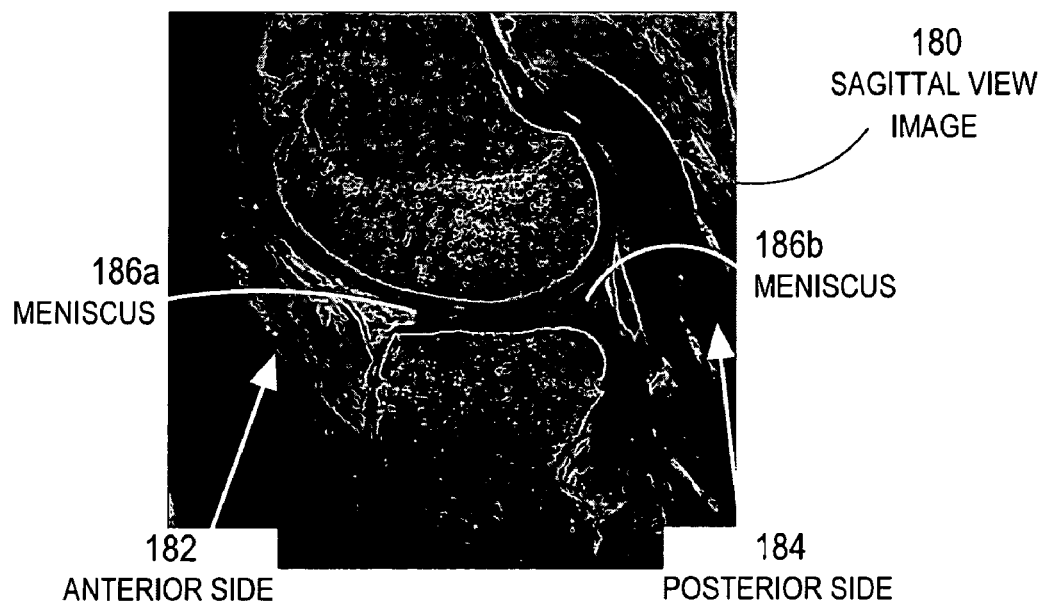
FIG. 1E is an image that illustrates an example sagittal view of scan data on one sagittal plane.

FIG. 1E is an image that illustrates an example sagittal view 180 of scan data on one sagittal plane. The superior side of the subject is up, and the anterior side 182 of the imaged knee is to the left, while the posterior side 184 is to the right. Small, triangular shaped dark areas of low intensity at the joint represent portions of the meniscus in this sagittal slice, including the anterior lateral meniscus 186a and the posterior lateral meniscus 186b.

FIG. 2 is a flow diagram that illustrates at a high level an example method 200 for automatically detecting meniscus tissue and meniscal tears, according to an embodiment. Although steps in FIG. 2 and subsequent flow charts, FIG. 3, FIG. 6 and FIG. 9, are shown in a particular order for purposes of illustration, in other embodiments, one or more steps may be performed in a different order or overlapping in time, in series or in parallel, or one or more steps may be omitted or added, or changed in some combination of ways.

In step 202 scan data from a scanning device is received. For example, scan data is received from scanner 140. In an illustrated embodiment, the scan data is received from a current MR scanner, but it is specifically anticipated that in other embodiments scan data is received from later generation MR imagers or other scanning devices. In the illustrated embodiments, scan data was received for subjects scanned using either Siemens Avanto 1.5-T MR or a Siemens Esprit 1.5-T scanner. An 8-channel extremity coil was used. Sagittal T1-weighted sequences (TR=580-800 ms, TE=10-20 ms) and a 512×512 were used. Meniscal tears can be diagnosed on both T1 and proton density MR images from this equipment.

Any method may be used to receive this data. For example, in various embodiments, the data is retrieved from a local file or database, or is sent from a different node on the network, either in response to a query or unsolicited, or the data is received using some combination of these methods.

In step 230, a region of interest (ROI) in the scan data is determined without human intervention based on historical use of scanning device. The region of interest is a subset of the scan data that includes scan elements that correspond to meniscus tissue and the vicinity thereof. In some embodiment, the ROI is determined by a human analyst and step 230 is replaced with a different step for receiving data that indicates the ROI. In some embodiments other parameters are also determined or received in this step, such as meniscus size and shape ranges and tear threshold scores, described in more detail below. Any method may be used to receive the ROI data or the historical data that indicates a ROI or other parameters. For example, in various embodiments, the data is included as a default value in software instructions, is received as manual input from an analyst or technician on the local or a remote node, is retrieved from a local file or database, or is sent from a different node on the network, either in response to a query or unsolicited, or the data is received using some combination of these methods. A particular embodiment of step 230 is described in more detail in a following section, with reference to FIG. 3, FIG. 4, FIG. 5A and FIG. 5B.

In step 240, an intensity threshold, called a meniscus extraction threshold that distinguishes the scan elements that correspond to the meniscus from surrounding tissue, is determined automatically, without human intervention, based on the region of interest. For current MR scan data in which the meniscus is represented by scan elements with the lowest intensities, the threshold is an upper threshold. In other scanning devices in which the meniscus tissue is represented by scan elements with the highest intensities, the threshold is a lower threshold. In still other embodiments, in which the meniscus tissue is represented by scan elements with intermediate intensities, the threshold is a matched pair of upper and lower thresholds. In the illustrated embodiment, the meniscus extraction threshold is adaptively determined for each set of scan data to allow for observed differences in thresholds among different devices and operators. A particular embodiment of step 240 is described in more detail in a following section, with reference to FIG. 6. In some embodiments, a human analyst determines the meniscus extraction threshold of the scan data, and step 240 is omitted.

It is noted here that many scan elements that do not represent meniscus tissue are also indicated by the threshold, and so in the illustrated embodiments, meniscus-like objects are defined. The meniscus extraction threshold determined in step 240, according to these embodiments, produces the maximum number of meniscus-like objects, when summed over all slices that span the ROI. As used herein, an object is a contiguous set of scan elements with intensities within the threshold (below an upper threshold, or above a lower threshold, or between a lower threshold and upper threshold of a matched pair). A meniscus-like object is an object that satisfies geometrical constraints for meniscus, such as falling within a particular size range or shape range or both. An embodiment of step 240 defining meniscus-like objects is described in more detail below with reference to FIG. 6.

In step 250, a meniscus object portion of the scan data is determined automatically, without human intervention, based on the meniscus intensity threshold. In embodiments in which the meniscus extraction threshold was determined based on the number of meniscus-like objects, these objects were already determined. In the illustrated embodiment, the meniscus object portion of the scan data includes not just the scan elements of the meniscus-like object but all scan elements in a minimum convex mask that encompasses the meniscus-like object. A particular embodiment of step 250 is described in more detail in a following section, with reference to FIG. 6, FIG. 7, and FIG. 8. In some embodiments, a human analyst determines the meniscus object portion of the scan data, and step 250 is omitted.

In step 260, the meniscus object portion of the scan data is examined to determine a propensity for meniscal tears, without human intervention, based on the meniscus extraction threshold. In some embodiments, a score proportional to propensity for tears is determined. In some embodiments, a tear/no-tear decision is made during step 260 for each of one or more divisions of the meniscus (e.g., medial/lateral/anterior/posterior). As used herein a propensity for tears is indicated by any data that visualizes, summarizes or measures bright, non-cartilage pixels in a meniscus object portion of scan data, including gray scale images, color images, binary images, scores, weighted scores, combined scores, and tear/no tear decisions, as described in more detail below. A particular embodiment of step 260 is described in more detail in a following section, with reference to FIG. 9, FIG. 10, and FIG. 11. In some embodiments, a human analyst reviews the scan data in the meniscus object portion to determine tear propensity, and step 260 is omitted.

In step 270, data that indicates the propensity for tears is presented to a user. For example the pixels in the meniscus object portion of the scan data is presented to a user. In various embodiments, data indicating the score or tear/no-tear decision or both is also presented during step 270. A particular embodiment of step 270 is described in more detail in a following section, with reference to FIG. 12.

2. Determining Region of Interest (ROI)

FIG. 3 is a flow diagram that illustrates at a high level an example method 300 for automatically determining a region of interest, according to an embodiment. Thus, method 300 is a particular embodiment of step 230.

In step 302, a size of an area of interest (AOI) is selected that is useful for detecting the meniscus in one slice of the scan data of the type received in step 202. For example, based on experience with sagittal slices where the meniscus is prominent (see, e.g., FIG. 8A described below) a historically useful area is about three centimeters (cm, 1 cm=$10^{-2}$ meters) vertically by five and a half centimeters horizontally, which is sufficient to encompass the knee joint where the meniscus is found. For current MR scanners, with pixel size of 0.3125 mm, an appropriate AOI is 100 rows by 180 columns of pixels, for an area of 3.125 cm by 5.625 cm (see, e.g., AOI 812 in FIG. 8A).

In step 304, an initial set of sagittal slices with historically prominent views of the meniscus is selected. Analysis of tears by a human analyst is historically performed using sagittal slices where the meniscus is clearly seen with sufficient area to detect tears. The inventors determined that the locations of meniscal tissue relative to the imaged volume tend to be stable when a uniform acquisition protocol is utilized, as is currently standard procedure. The inventors have determined that most useful sagittal slices are those that depict portions of the subject's knee from about 20% to about 35% of the distance across the knee from either the lateral or medial side. Thus, in an illustrated embodiment, the initial set of sagittal slices are located from about 20 percent to about 35 percent of a distance between an outside pair of sagittal planes that are each tangent to a different outer surface of the knee of the subject. This distance corresponds to about 20% to about 35% of the total number N of sagittal slices that span the knee.

Figure 4:
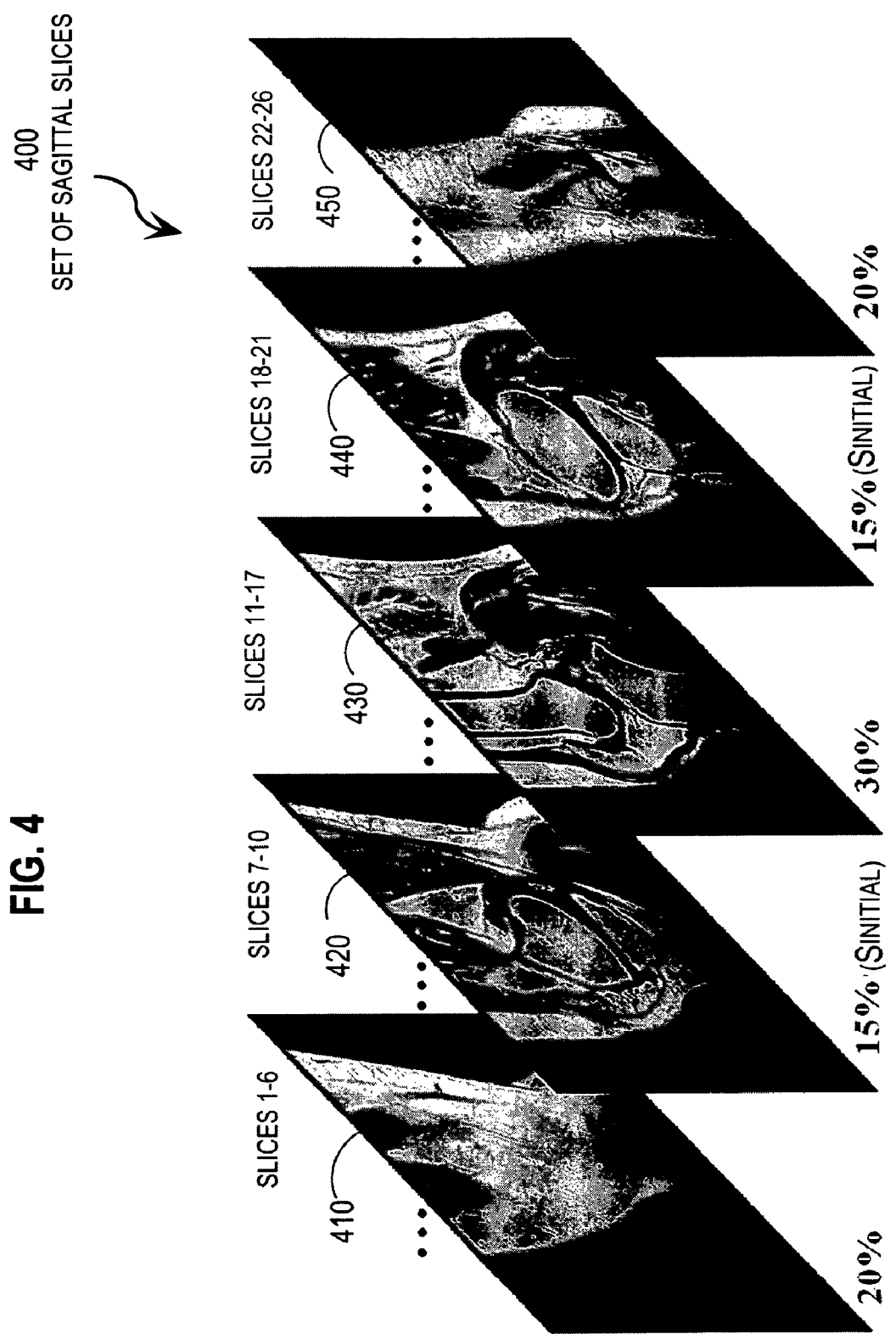
FIG. 4 is a diagram that illustrates groupings of sagittal slices in scan data, according to an embodiment.

FIG. 4 is a diagram that illustrates groupings of sagittal slices 400 in scan data, according to an embodiment. In the illustrated embodiment, there are 26 slices that span a subject's knee from the first medial slice (slice 1) to the last lateral slice (slice 26). Each slice therefore represents less than 4% of the total. The first approximately 20% of the sagittal slices that span the knee are slices 1 to 6, with representative image 410. The next 15% (which are historically prominent and therefore in the initial set) are slices 7 to 10, with representative image 420. The next approximately 30% of the sagittal images (which are not in the initial set) are slices 11-17, with representative image 430. The next 15% (which are historically prominent and therefore in the initial set because of their distance from the last medial slice, 26) are slices 18 to 21, with representative image 440. The last approximately 20% of the sagittal slices that span the knee are slices 22 to 26, with representative image 450. Thus sagittal slices 7-10 and 18-21 are selected for the initial set in the illustrated embodiment. The number Ninitial of slices in the initial set (e.g., 8 in the embodiment illustrated in FIG. 4) is less than N (e.g., 26 in the illustrated embodiment).

In step 310, a mean image is determined for the sagittal slices in the initial set. Each mean scan element in the mean image is based on an average of intensity values in corresponding scan elements in the initial set of sagittal slices of the scan data. This relationship is indicated by Equation 1.

$$M(i,j) = \text{mean}_{k \in Sinitial}\{I_k(i,j)\} \quad (1)$$

Where i is an index that indicates a row of a pixel and j is an index that indicates a column of a pixel and k is an index that indicates a sagittal slice, $1 \leq k \leq N$ where the pixel is located. $I_k$ is the 2-D image of the kth slice. Sinitial indicates k values for the initial set (e.g., 7-10 and 18-21) of sagittal slices, and $\epsilon$ indicates values that are elements of the following set. M is the resulting mean image. Thus the operation indicated by Equation 1 is performed on a pixel by pixel basis only for the slices that are in the initial set of sagittal slices. Note that $I_k$, and therefore M, is in general larger than the size of the AOI received in step 302, because the purpose of M is to determine where to center an AOI of the size received in step 302.

In step 320, a band of extreme intensity is determined in the mean image to center an AOI. For example, for scan data in which the meniscus is a minimum in intensity, as in current MR scan data, the extreme is a minimum. In other embodiments, the meniscus is associated with a maximum intensity, and the extreme is a maximum. As used herein, an extreme intensity is a minimum intensity or a maximum intensity. In some embodiments a meniscus is not associated with an extreme intensity, and steps 312 and 314 are omitted.

Figure 5A:
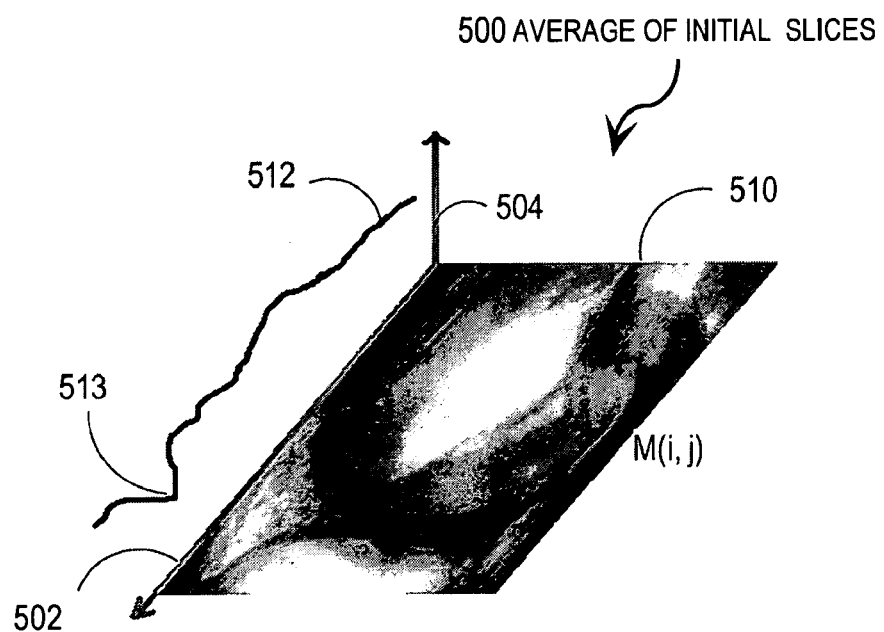
FIG. 5A and FIG. 5B are diagrams that illustrate use of a mean image for determining a center for an area of interest (AOI), according to an embodiment.
Figure 5B:
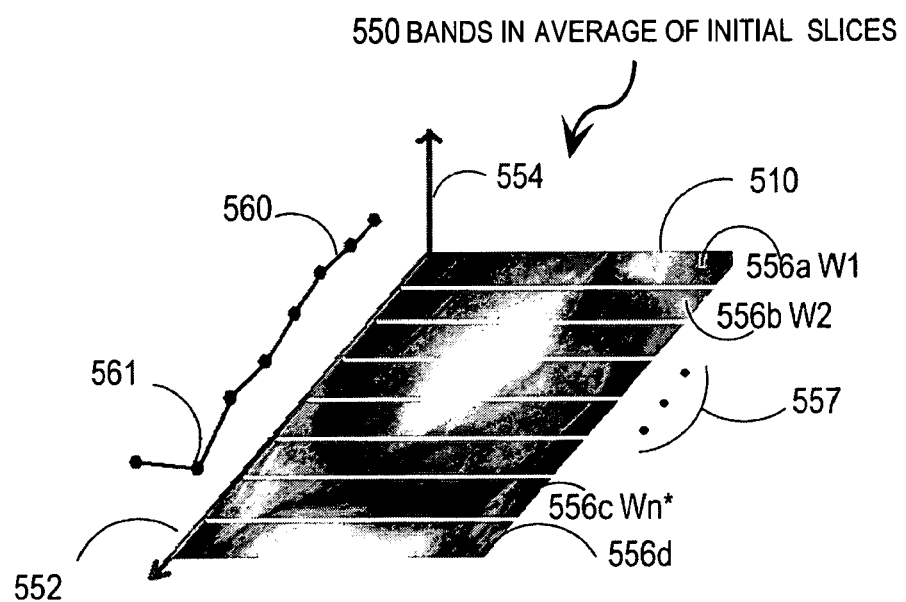

FIG. 5A and FIG. 5B are diagrams that illustrate use of a mean image for determining a center for an area of interest (AOI), according to an embodiment. FIG. 5A is a diagram 500 that illustrates properties of the average image M 510 presented in perspective as if lying horizontally. Horizontal axis 502 is row number and vertical axis 504 indicates average intensity in a row across all columns in the AOI size. For example, in the illustrated embodiment, the average image width is the entire sagittal image, which is larger than the AOI size of 180 columns (5.625 cm). In some embodiments the 180 columns of the AOI are less than the entire sagittal slice, and the 180 middlemost columns of a sagittal slice, relative to the anterior and posterior surfaces of the subject, are used. In some embodiments, the vertical axis 504 is average intensity across all columns in the sagittal slice, e.g., 512 columns, even beyond the AOI column size (e.g., 180 columns). In some embodiments, the vertical axis indicates total intensity by summing all columns in a given row.

The trace 512 shows how average/total pixel intensity in a row varies with row. A minimum 513 occurs at rows near the vertical center of the meniscus. Thus a row near the minimum 513 is selected as a center row of an AOI having the historical size (e.g., 100 rows by 180 columns).

In some embodiments, to reduce the effects of noisy data, or for computational efficiency, the mean image M is divided into a number $N_B$ of bands $W_n(ij)$ ($1<n<N_B$) that have small height relative to the AOI row size, and the average (or total) intensity is determined for each band of rows. In an illustrated embodiment the band height is 16 rows. Since the band height (e.g., 16 rows) is small compared to the AOI row size (e.g., 100 rows), an AOI centered on the center row of a band is still likely to encompass the meniscus and tissues in the immediate vicinity of the meniscus. FIG. 5B is a diagram 550 that illustrates properties of bands of the average image M 510. Horizontal axis 552 is band number and vertical axis 554 indicates average (or total) intensity in a band. FIG. 5B depicts band $W_1$ 556a, $W_2$ 556b, $W_{n*}$ 556c, and following band 556d, as well as intervening bands indicated by ellipsis 557. The trace 560 shows how average/total pixel intensity in a band varies with band number. A minimum 561 occurs at a band near the vertical center of the meniscus. Thus a row near the center of the band with minimum 561 is selected as a center row of an AOI having the historical size (e.g., 100 rows by 180 columns). The band with minimum 561 is designated herein as $W_{n*}$ 556c and the selection of n* is given by Equation 2

$$n^*=\arg[\min_{n\in(1,NB)}\{\text{mean}(W_n)\}] \quad (2)$$

where min indicates the operation of selecting the minimum value over the following set of values, and arg indicates the operation of selecting the argument (or sequence number) corresponding to the member of the set selected by the min operation.

In step 314, an area of interest (AOI) is centered on an extreme row, such as a center row of a band of extreme intensity. The subset of the images $I_k$ in the area of interest centered on the minimum row, or band $W_{n*}$, is indicated as $I_k^{AOI}$.

In some embodiments, the scan elements included in a volume of interest (VOI) are simply the $I_k^{AOI}$ for k∈Sinitial. However, in an illustrated embodiment, the full set of sagittal slices is reconsidered for contributing scan elements to the VOI. According to these embodiments, method 300 includes step 320 and step 322.

In step 320 a template φ is determined based on the average intensity in the pixels in the AOI over the initial set of sagittal slices. For example, in an illustrated embodiment, step 320 is performed using Equation 3.

$$\phi(i,j)=N\text{initial}^{-1}\tau_{k\in Sinitial}I_k^{AOI}(i,j) \quad (3)$$

In step 322 a final set of sagittal slices with k values indicated by Sfinal is determined. The slices in the final set show small deviations in the AOI from the template. Any method may be used to measure the deviation from the template. In an illustrated embodiment, a mean square error (MSE) is used as the measure of deviation. For example, in an illustrated embodiment, step 320 is performed using Equation 4a and Equation 4b and Equation 4c.

$$MSE_k=\Sigma_{i,j}(I_k^{AOI}(i,j)-\phi(i,j))^2 \quad (4a)$$

and $$MSE_{max}=\max_{k\in(1,N)}\{MSE_k\} \quad (4b)$$

and $$\text{if } (MSE_k\leq 0.25*MSE_{max}) \text{ then } k\in S\text{final} \quad (4c)$$

In other embodiments a different fraction of $MSE_{max}$, or a different measure of deviation, is used to determine membership in Sfinal.

In step 330, a volume of interest (VOI) is determined as a union of the AOI from all slices in the final set of sagittal slices. This can be defined in Equation 5a.

$$I^{VOI}(i,j,k)=\cup_{k\in Sfinal}I_k^{AOI}(i,j) \quad (5a)$$

In some embodiments, the volume of interest includes just one slice, and is identical to an AOI. The term region of interest (ROI) is used herein to refer to an AOI or VOI or both, depending on context.

3. Meniscal Extraction

Meniscal extraction is a process that separates menisci from other structures of the knee after the ROIs have been defined. MR images acquired from different medical centers and vendors may have significant variations in intensities, and it is advantageous to make the meniscus extraction adaptive to such intensity variations. In an illustrated embodiment, the threshold for the meniscal extraction is adjusted and estimated automatically for each case, as indicated by step 240 in FIG. 2.

FIG. 6 is a flow diagram that illustrates at a high level an example method 600 for automatically detecting meniscus tissue, according to an embodiment. Method 600 is a particular embodiment of step 240 and step 250 in FIG. 2. Method 600 is based on a region of interest (ROI). In some embodiments, the ROI is provided by a human analyst. In some embodiments, the ROI is determined according to the method 300, described above.

In step 602, an average intensity, μ, is determined in the ROI. For example, μ is determined using Equation 5b.

$$\mu=(N\text{final}*Ni*Nj)^{-1}\Sigma_{k\in Sfinal}\Sigma_i\Sigma_j I_k^{AOI}(i,j) \quad (5b)$$

where Nfinal is the number of slices in the final set of sagittal slices, Ni is the number of rows in the AOI (e.g., 100) and Nj is the number of columns in the AOI (e.g., 180).

During step 602 a next candidate threshold $\tau_m$ (m=1, Nτ, where Nτ is the number of candidate thresholds to be tried) is also determined based on μ. For example, for scan data in which the meniscus is a minimum, the candidate threshold is an upper threshold that is a fraction less than one of μ. For scan data in which the meniscus is a maximum, the candidate threshold is a lower threshold that is a numeric factor of μ that may be less than, equal to or greater than one times μ. For scan data in which the meniscus is a middle intensity, the candidate threshold is a matched pair of lower and upper candidate thresholds that are each a numeric factor of μ. In an illustrated embodiment, the next candidate threshold is a first upper threshold $\tau_1$ equal to 0.2*μ.

In step 610, the pixels within the candidate threshold are determined. For example, a binary image is generated from the AOI in each slice of the final set, in which each pixel with an intensity within the candidate threshold is given one of two binary values (e.g., 1) and each pixel outside the candidate threshold is given a different one of the two binary values (e.g., 0). A pixel intensity is within a threshold, as used herein, if the intensity is less than or equal to an upper threshold, greater than or equal to a lower threshold, or in a range of a matched pair of upper and lower thresholds, inclusive.

Figure 7A:
FIG. 7A through FIG. 7D are image portions that depict scan elements associated with an object based on a particular threshold value, according to an embodiment.

During step 610 objects are also determined in each image of the final set of slices. As used herein, an object is a contiguous set of scan elements within the candidate threshold. FIG. 7A through FIG. 7D are image portions that depict scan elements associated with an object based on a particular threshold value, according to an embodiment. FIG. 7A depicts an object 710, in which dark pixels are pixels with an intensity within a threshold intensity, e.g., below an upper threshold $\tau_m$.

As stated above, not all objects are meniscus-like objects. A meniscus-like object is an object that satisfies geometrical constraints for meniscus, such as falling within a particular size range or shape range or both. In various other embodiments other geometrical constraints are included, such as depth, as determined by a number of adjacent slices in which the object appears.

In step 612, objects that fall within a meniscus-like size range are determined. Any method may be used to determine a meniscus-like size range. In an illustrated embodiment, a meniscus-like size range is an area between about 5 mm² (about 50 pixels) and about 80 mm² (about 800 pixels) on one sagittal slice. Objects with smaller areas are considered noise and objects with larger areas are considered to be non-meniscus structures. The values of the size range are received by the process, e.g., during step 230 while receiving historical information, using any method known in the art. It is assumed for purposes of illustration that object 710 falls within the meniscus-like size range.

Figure 7B:
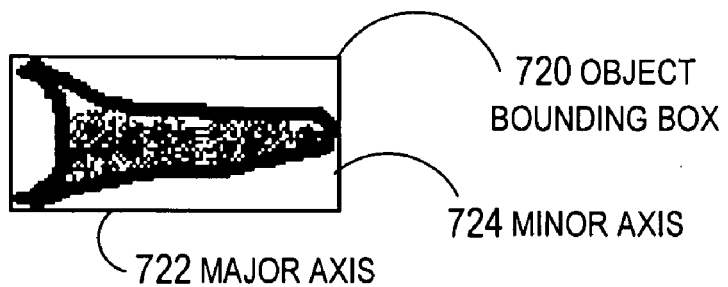

In step 614, objects that fall within a meniscus-like shape range are determined. Any method may be used to determine a meniscus-like shape range. In an illustrated embodiment, a meniscus-like size range is a range of aspect ratios, where an aspect ratio is a ratio of a major axis length divided by a minor axis length. The major axis is the longest dimension of the object, and the minor axis is the longest dimension perpendicular to the major axis. In some embodiments, the aspect ratio is approximated by the ratio of the major axis and minor axis of a bounding box. The bounding box is the rectangle in row/column space that extends from the smallest to largest row number and smallest to largest column number of scan elements in the object. When the object's major axis is aligned with a row or column, the aspect ratio of the bounding box is the same as the aspect ratio of object. When not, the bounding box aspect ratio is more compact (closer to one). FIG. 7B shows an object bounding box 720 for object 710, and a box major axis 722 and minor axis 724. Since object 710 has a major axis that is about parallel to the image rows, the aspect ratio of the bounding box 720 is about the same as the aspect ratio of the object 710.

Figure 7C:
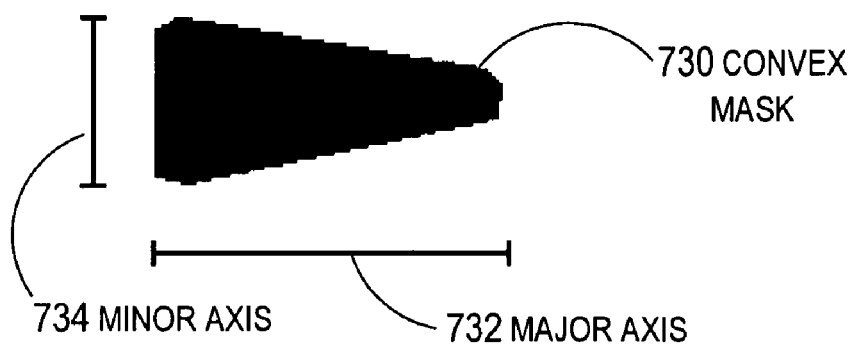

In some embodiments, the major and minor axis length determinations are made simpler by first forming a convex mask for the object. In such embodiments, method 600 includes step 616 to form a convex mask from each remaining object that satisfies meniscus-like size and shape constraints. A convex mask is a minimum convex shape that encompasses all pixels in the object. A convex mask is one in which every line segment connecting points in the mask is entirely within the mask. FIG. 7C depicts a convex mask 730 for object 710. Any method known in the art may be used to form a convex mask of the object. FIG. 7C also depicts a major axis 732 and minor axis 734 of the convex mask. These axis lengths are substantively equal to the major and minor axes of the original object 710.

Figure 7D:
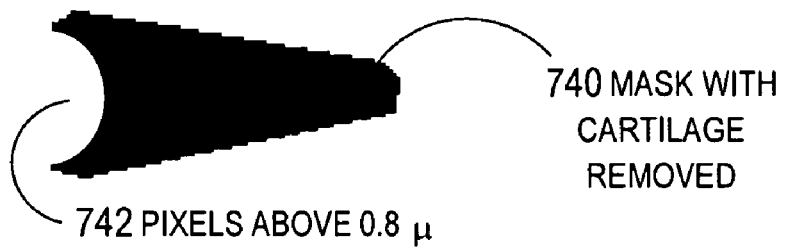

It is noted here that in a later step, cartilage tissue is to be distinguished from meniscus. This is easily done with a cartilage lower threshold, e.g., 0.8*μ. The convex mask may include pixels that represent cartilage tissue, but such pixels can be removed using the cartilage threshold. FIG. 7D depicts a revised mask 740 with cartilage removed by removing pixels 742 with intensity above 0.8*μ. However, during step 616, cartilage is not routinely removed. In some embodiments, step 616 is omitted while determining the meniscus intensity threshold.

In an illustrated embodiment, a meniscus-like shape range is an aspect ratio between about 1 and about 6 for the actual major and minor axis, or about 1 and about 5 for the bounding box. Objects with other aspect ratios are considered to be non-meniscus structures because they are too elongated (aspect ratio too large) or too compact (aspect ratio substantively equal to 1). The values of the shape range are received by the process, e.g., during step 230 while receiving historical information, using any method known in the art.

In step 620, the number of meniscus-like objects ($N_{MLO}$) in the ROI for the given threshold $\tau_m$ is determined by adding the number of meniscus-like objects in each slice over all the slices in the final set, as given by Equation 6a.

$$N_{MLO}(\tau_m) = \tau_{k \in Sfinal} N_{MLO}(k, \tau_m) \qquad (6a)$$

Where $N_{MLO}(k, \tau_m)$ is the number of meniscus-like objects using threshold $\tau_m$ on the kth slice.

In step 630, it is determined whether the current candidate threshold $\tau_m$ is less than some maximum candidate threshold (e.g., a cartilage threshold about 0.8*μ). If so, another candidate threshold $\tau_{m+1}$ can be tried; and control passes to step 632. In step 632 the index m is incremented by one and the candidate threshold $\tau_m$ is incremented, e.g., by 0.05*μ in the illustrated embodiment. Control passes back to step 610 and following to determine $N_{MLO}$ for the next candidate threshold $\tau_{m+1}$.

If it is determined in step 630 that the current threshold is greater than or equal to the maximum candidate threshold, control passes to step 640 to determine the best of the Nτ candidate thresholds. For example, in the illustrated embodiment, $N_{MLO}(\tau)$ is determined using Equation 6a for 12 thresholds (Nτ=12): $\tau_m$=0.20*μ, 0.25*μ, . . . , 0.75*μ for m=1, 12, respectively.

In step 640, τ* is determined that gives a greatest number of meniscus-like objects, as expressed in Equation 6b.

$$\tau^* = \arg[\max_{m=1,N\tau}\{N_{MLO}(\tau_m)\}] \qquad (6b)$$

This value of τ* is the meniscus extraction threshold for the ROI and is associated with index m*.

In step 642, the convex masks are determined for the meniscus-like objects using meniscus extraction threshold τ*. In some embodiments that include step 616, the convex mask is already determined and are simply retrieved for the selected index m*. In some embodiments, step 616 is omitted, and the convex masks are determined during step 642 for the objects associated with index m* on each slice in the final set. In some embodiments, step 642 includes removing scan elements associated with cartilage, e.g., by removing scan elements with intensities above a cartilage threshold (e.g., about 0.8*μ).

The resulting, cartilage-removed masks (e.g., mask 740 in FIG. 7D) for the final set of slices constitute a meniscus object portion of the scan data.

Figure 8A:
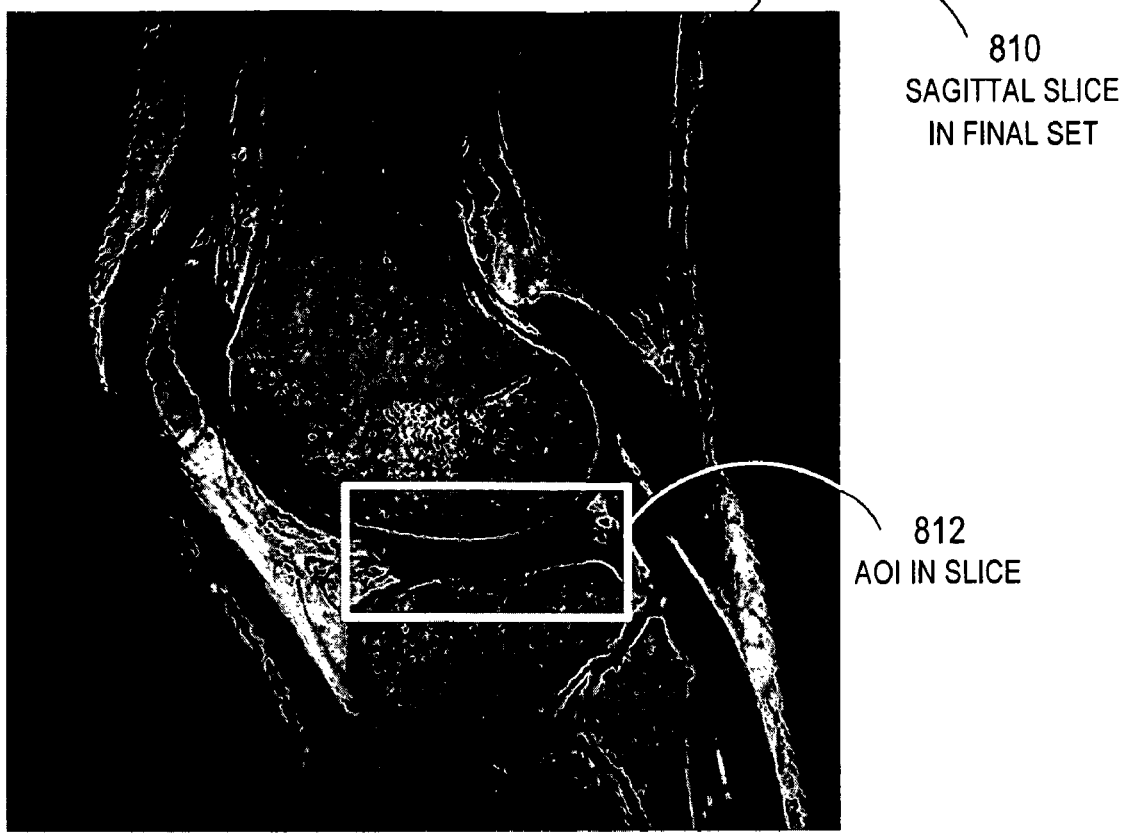
FIG. 8A through FIG. 8J are image portions that depict results after intermediate steps of the method of FIG. 6, according to an embodiment.
Figure 8B:
Figure 8C:
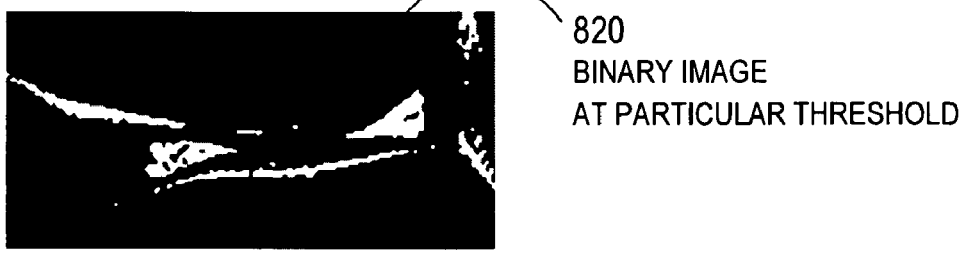

FIG. 8A through FIG. 8J are image portions that depict results after intermediate steps of the method of FIG. 6, according to an embodiment. FIG. 8A depicts a sagittal slice 810 in final set and the AOI 812 on the slice. FIG. 8B depicts a magnified view of scan data intensities in the AOI 812. FIG. 8C depicts a binary image 820 in the AOI for a particular threshold $\tau_m$. The pixels below the upper threshold $\tau_m$ are assigned one binary value (e.g., 1) and are shown in white. The non-meniscus pixels above the upper threshold $\tau_m$ are assigned the other binary value (e.g., 0) and are shown in black.

Figure 8D:

FIG. 8D depicts a binary image 830 like FIG. 8C but removing pixels (e.g., assigning pixel values=0) in objects outside the meniscus-like size range. Two long thin objects and two triangular objects remain. The long thin objects have aspect ratios above 6 and are removed using the meniscus-like shape range of aspect ratios.

Figure 8E:
Figure 8F:

FIG. 8E depicts a binary image 840a in a bounding box of a first triangular object within the meniscus-like shape range. FIG. 8F depicts a binary image 840b in a bounding box of a second triangular object within the meniscus-like shape range. As can be seen, some pixels inside both objects are above the upper threshold $\tau_m$ and appear black.

Figure 8G:
Figure 8H:

FIG. 8G depicts a binary image 850a in a bounding box of a first convex mask minimally encompassing the first object. FIG. 8H depicts a binary image 850b in a bounding box of a second convex mask minimally encompassing the second object. It is assumed for purposes of illustration that neither mask includes high intensity cartilage pixels; and so neither mask has interior pixels removed. If the threshold used to generate the convex masks in FIG. 8G and FIG. 8H is the meniscus extraction threshold $\tau^*$, then the white pixels represent the meniscus object portion of the scan data on this slice.

Figure 8I:
Figure 8J:

FIG. 8I depicts an image 860a in a bounding box of a first convex mask, with scan data intensities inside the convex mask, produced for example by multiplying the original intensities in the scan data by the binary image values of the convex mask. FIG. 8J depicts an image 860b in a bounding box of a second convex mask, with scan data intensities inside the convex mask.

Bright areas evident in the masked scan data may be indicative of tear or tear propensity in the meniscus objects in this slice.

4. Determining Tear Propensity

FIG. 9 is a flow diagram that illustrates at a high level an example method 900 for automatically determining a propensity for meniscal tears, according to an embodiment. In step 902 tear categories or tear threshold scores or both are defined. A tear category and a tear score are based on the distribution of intensity values in the meniscus object portion of the scan data. The tear threshold score is a tear score that has been associated with meniscal tears in historical data. In the illustrated embodiment, the tear categories and tear threshold scores are pre-defined and merely received during step 902.

Any method may be used to define a tear category or tear score, including any statistic of intensity value distribution in the meniscus object portion of the scan data, such as mean intensity, standard deviation, skewness, kurtosis, alignment or any other property of the intensity values in the portion, alone or in combination.

In an illustrated embodiment, described in more detail below, three categories of tears and two statistics of intensity distribution based on those categories, called breakability and degeneracy metrics, are defined. A total score combining the two metrics on multiple adjacent slices is also defined. For these definitions, a tear threshold score is determined that varies with quadrant of meniscus tissue. In the illustrated embodiment, a tear is associated in the historical data with combined scores at or above the predefined thresholds given in Table 1.

TABLE 1

Example Tear Threshold Scores in meniscus quadrants.

| Quadrant | Tear Threshold Score |
| --- | --- |
| Anterior medial meniscus | 90 |
| Posterior medial meniscus | 70 |
| Anterior lateral meniscus | 95 |
| Posterior lateral meniscus | 80 |

In various embodiments, values of the tear threshold scores are received in any manner known in the art, such as described above.

Figure 10A:
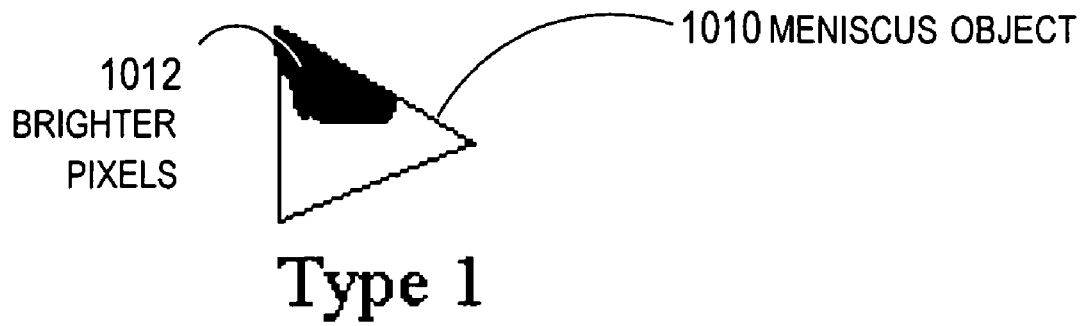
FIG. 10A through FIG. 10C are block diagrams that illustrate types of meniscal damage, according to an embodiment.
Figure 10B:
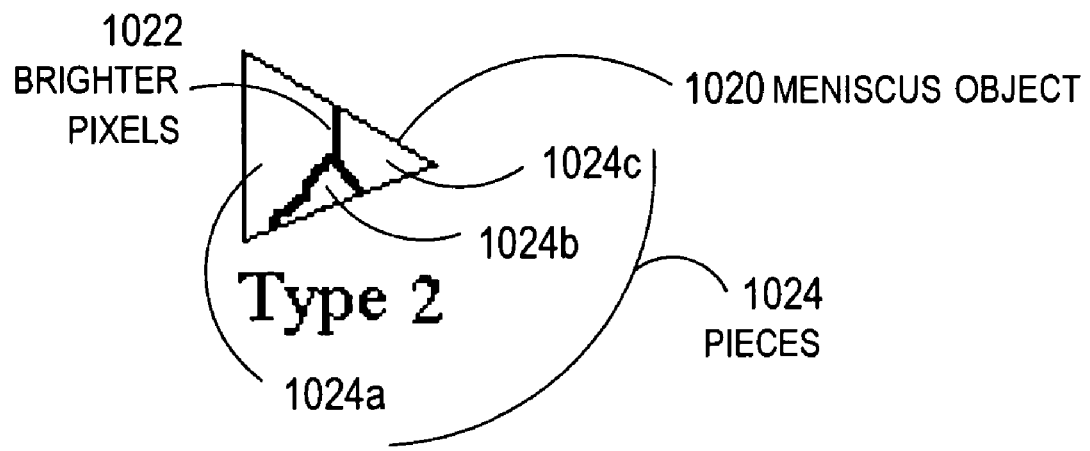
Figure 10C:
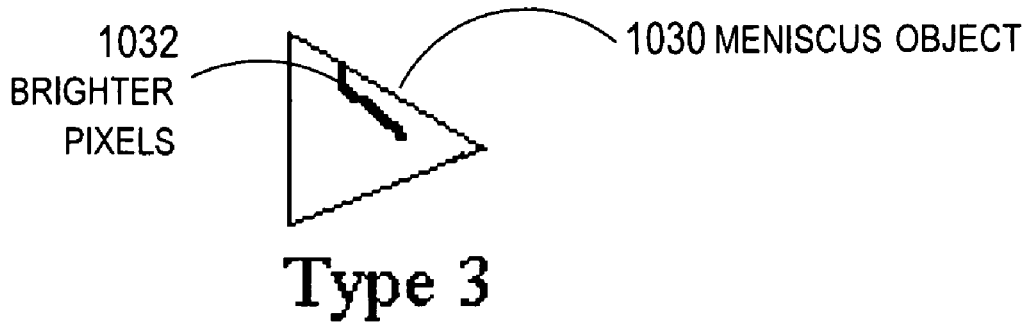

The inventors designed two statistics (also called metrics) to reflect three categories of tears pertinent to the clinical decision to initiate surgery. FIG. 10A through FIG. 10C are block diagrams that illustrate types of meniscal damage, according to an embodiment. FIG. 10A depicts Type 1 damage in which a meniscus object 1010 includes a compact area of brighter pixels 1012 (that are not above the cartilage threshold). Type 1 is most commonly seen in adult and elderly individuals and relates to the solidity of the meniscus. FIG. 10B depicts Type 2 tear damage in which a meniscus object 1020 is divided into two or more separate regions by a linear arrangement of brighter pixels 1022 (that are not above the cartilage threshold). Type 2 is a tear that breaks the meniscus into multiple pieces. FIG. 10C depicts Type 3 tear damage in which a meniscus object 1030 is not divided into separate regions by a linear arrangement of brighter pixels 1032 (that are not above the cartilage threshold). Type 3, the most common type of acute tear, is characterized by a linear rent that reaches an articular surface of the meniscus, and has the potential to become a type 2 tear if not treated surgically. An articular surface of the meniscus articulates with the cartilage of the tibia or femur. Type 2 and 3 tears are most often seen in young athletes.

Breakability is a measure reflecting a change from the meniscus extraction threshold that, when used as a threshold, fragments the extracted meniscus object into more than one piece. Breakability is a measure of the similarity to Type 2 and Type 3 tears. A procedure to determine breakability is described in more detail below with respect to step 920.

Degeneracy is a measure reflecting a change from the meniscus extraction threshold that, when used as a threshold, significantly changes the portion of the object below the threshold. Degeneracy is a measure of the similarity to Type 1 damage. A procedure to determine degeneracy is described in more detail below with respect to step 930.

The inventors developed a combined score based on both metrics, as described in more detail below. From historical data, the inventors determined that most tears occur in the posterior horn of the medial meniscus, followed in frequency by tears in the posterior horn of the lateral meniscus. Tears in the anterior quadrants of both medial and lateral menisci are more rare. Using a training set of 10 historical cases, 5 positive (tears) and 5 negative (no tears), the different tear threshold scores of Table 1 were determined for four meniscus quadrants. Thus in step 910, a particular one of the anatomical quadrants of the meniscus is selected for scoring meniscal tear propensity. In some embodiments, the meniscus score is not divided in quadrants and step 910 is omitted or replaced with a different set of anatomical divisions of the meniscus (e.g., anterior and posterior only, or more than four divisions of the meniscus).

In step 920, a breakability measure is determined based on largest breaking fraction of multiple fractions of the meniscus threshold intensity $\tau^*$. As defined herein, a breaking fraction $f_B$ of $\tau^*$ is one that, when $f_B \tau^*$ is used as a threshold, divides the meniscus object portion into multiple distinct portions called pieces. In other embodiments, with meniscus intensities at an intermediate or maximum compared to other tissues, different probe numeric factors are used to determine breakability.

For example, in an illustrated embodiment, the multiple probe fractions $f_p$ of the meniscus threshold intensity considered to find breaking fractions are five probe fractions (p=1, 5) descending from 0.7 to 0.3 in steps of 0.1. The smaller the fraction, the more likely that the meniscus object will be broken into multiple pieces. The largest fraction that causes the break, is the largest breaking fraction. In the illustrated embodiment, a score is associated with each fraction, as shown in Table 2. In the illustrated embodiment, the list of probe fractions begins from 0.7 (index p=1) instead of other higher probe fractions (e.g., 0.9, 0.8) to differentiate the breakability threshold from the meniscus extraction threshold (f=1). The score starts at 90 and not a higher score to put an appropriate weight on the breakability measurement without overemphasizing it. In general, a breaking fraction is determined from among a number Np probe fractions $f_p$.

TABLE 2

Example probe fractions $f_p$ of meniscus threshold intensity $\tau^*$.

| Index p | $f_p$ | Breakability score |
|---|---|---|
| 1 | 0.7 | 90 |
| 2 | 0.6 | 70 |
| 3 | 0.5 | 50 |
| 4 | 0.4 | 30 |
| 5 | 0.3 | 10 |

Any method may be used to determine if a particular probe fractions divides the meniscus object into multiple pieces. Methods well known in the art for determining if two pixels are connected (do not cross a pixel above the threshold) include connected component labeling and blob analysis. (See for example, Gonzalez and Woods, *Digital Image Processing*, $2^{nd}$ *Edition*, Prentice Hall, Upper Saddle River, N.J., ISBN 0201180758, 739 pp, 2002.)

The procedure for finding the index p* of the largest breaking fraction can be expressed with Equation 7a.

$$p^*(O_k) = \arg[\psi\{O_k, f_p \tau^*\} \geq 2, p=(1, Np)] \quad (7a)$$

where $O_k$ is a meniscus object on slice k∈Sfinal, and $\psi$ is a counting operation that determines how many pieces the meniscus object $O_k$ breaks into when threshold $f_p \tau^*$ is applied. The number p* is the first index p that causes the meniscus to break or, in other words, results in $\psi\{O_k, f_p \tau^*\} \geq 2$. Thus the largest $f_B = f_{p^*}$. A breakability score a is defined for the meniscus object $O_k$ using Equation 7b.

$$\alpha(O_k) = \text{Breakability score}\{p^*(O_k)\} \quad (7b)$$

In step 930, a degeneracy measure is determined based on decrease in area of the meniscus object portion within a threshold equal to a fraction $f_p$ of the meniscus extraction threshold for a number Np fractions, Np>1. In other embodiments, with meniscus intensities at an intermediate or maximum compared to other tissues, different probe factors are used to determine degeneracy.

For example, in an illustrated embodiment, this metric quantifies the rate with which the area of meniscal fragments below a threshold decreases as the threshold is lowered to various fractions of the meniscus intensity threshold. In this embodiment, the degeneracy metric β is given by Equation 8a and Equation 8b.

$$\xi_p = A(O_k, f_p \tau^*)/A(O_k, \tau^*) \quad (8a)$$

where $A(O,\tau)$ is the area of a meniscus object O on slice k∈Sfinal below a threshold $\tau$. Thus $\xi_p$ gives the ratio of the area below the probe threshold $f_p \tau^*$ to the original area of the meniscus object. Then $$\beta = \tau_{p=(1,Np)} 2^{-p} \xi_p \quad (8b)$$

The term $2^{-p}$ in Equation 8b gives more weight to a decrease in area attributed to the larger fractions.

If the meniscus extraction fails on a slice, the breakability and degeneracy scores are both set to 100. Both the breakability and degeneracy scores of those slices that do not belong to the final set are set to 0.

There are 4 possible combinations of outcomes when these metrics are applied. FIG. 11A through FIG. 11D are sequences of images that illustrate different types of infrastructure changes with threshold changes, according to an embodiment.

Figure 11A:
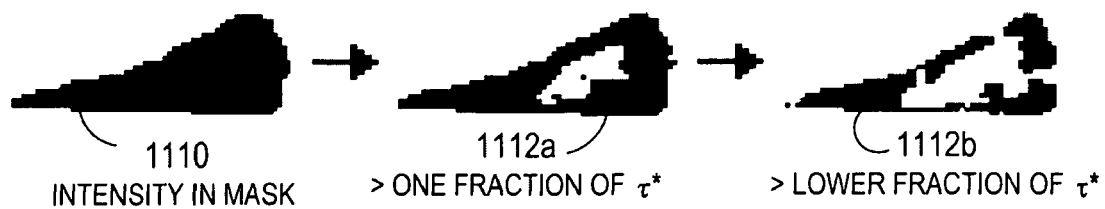
FIG. 11A through FIG. 11D are sequences of images that illustrate different types of infrastructure changes with threshold changes, according to an embodiment.

(1) Both breakability and degeneracy may be high, implying that the meniscus body has a significant amount of high-intensity pixels (degenerated pixels) and also that the meniscus is broken by high-intensity pixels. FIG. 11A depicts image portion 1110 of scan data intensity in mask of a meniscus object, a first binary image 1112*a* using a first fraction of the meniscus extraction threshold and a second binary image 1112*b* using a second, smaller fraction of the meniscus intensity threshold. Pixels within the threshold are black. A large area is removed with the first threshold and the meniscus breaks into multiple pieces at the second threshold. Both breakability and degeneracy are high.

Figure 11B:
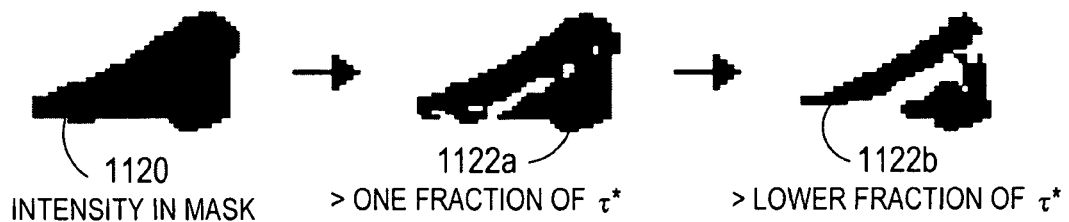

(2) Breakability may be high and degeneracy may be low, implying that the meniscus body is homogenous but that the meniscal shape is interrupted by high-intensity signals cutting through it. FIG. 11B depicts image portion 1120 of scan data intensity in a mask of a meniscus object, a first binary image 1122*a* using a first fraction of the meniscus extraction threshold and a second binary image 1122*b* using a second, smaller fraction of the meniscus intensity threshold. Pixels within the threshold are black. A smaller area is removed with the first threshold but a type 3 tear is apparent. At the next threshold a complete Type 2 tear is evident. Breakability is high and degeneracy is low.

Figure 11C:
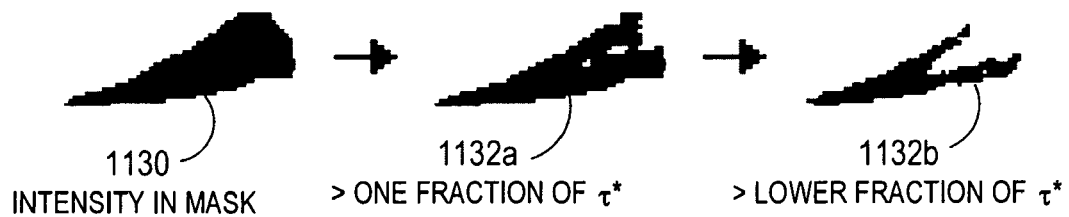
Figure 11D:
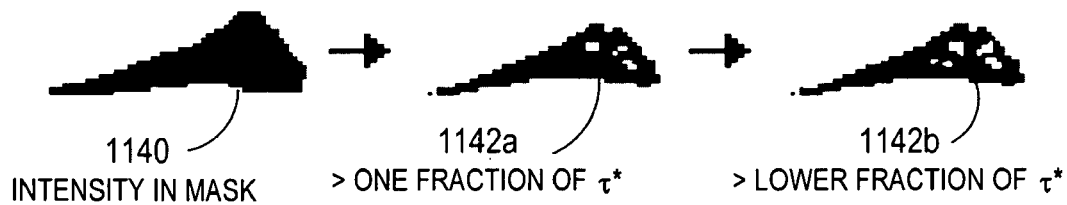

(3) Breakability may be low and degeneracy may be high, implying that the meniscus body is inhomogeneous, with a significant amount of high-intensity signals (degenerated pixels), but that the meniscal shape is not interrupted. FIG. 11C depicts image portion 1130 of scan data intensity in a mask of a meniscus object, a first binary image 1132*a* using a first fraction of the meniscus extraction threshold and a second binary image 1132*b* using a second, smaller fraction of the meniscus intensity threshold. Pixels within the threshold are black. A smaller area is removed with the first threshold but a larger area with the second threshold. However, the area below the lower threshold is still in one piece. Breakability is low and degeneracy is high.

(4) Both breakability and degeneracy may be low, implying that the meniscus body is homogenous and clear of many high-intensity signals. FIG. 11C depicts image portion 1140 of scan data intensity in mask of meniscus object, a first binary image 1142a using a first fraction of the meniscus extraction threshold and a second binary image 1142b using a second, smaller fraction of the meniscus intensity threshold. Pixels within the threshold are black. A smaller area is removed with both thresholds; and the area below the lower threshold is still in one piece. Breakability is low and degeneracy is low.

In step 940, a weighted sum of multiple degeneracy measures and multiple breakability measures on corresponding adjacent sagittal slices of the scan data are determined. The continuity of meniscal tears from one slice to the next is taken into account while calculating the average breakability and solidity scores for each slice. The inter-slice continuity of a positive decision (tear happens) is an important consideration in calling for a tear in the final decision. Tears that run through multiple slices have higher chances of being true tears than the tears seen only on a single slice. The final score of a single slice is therefore derived by using a weighted average over its neighboring slices in some embodiments.

In an illustrated embodiment, the weighted sum (bold) at slice k is given in Equation 9a and Equation 9b using three adjacent slices in Sfinal.

$$\alpha_k = 0.25\ \alpha_{k-1} + 0.5\ \alpha_k + 0.25\ \alpha_{k+1}\ (\text{for } k-1, k, k+1 \in S\text{final}) \quad (9a)$$

$$\beta_k = 0.25\ \beta_{k-1} + 0.5\ \beta_k + 0.25\ \beta_{k+1}\ (\text{for } k-1, k, k+1 \in S\text{final}) \quad (9a)$$

In other embodiments, more slices or different weights or both are used in defining the weighted sum. In some embodiments, a weighted sum is not performed and step 940 is omitted.

In step 942 a combined score based on both breakability and degeneracy is determined. Because breakability and degeneracy metrics capture information about specific types of tears, if $\alpha_k$ is significantly larger than $\beta_k$ in any given slice, this implies that the tear may be a type 1 or type 2 tear. If $\beta_k$ is significantly larger than $\alpha_k$, type 1 damage is more likely. If great enough, type 1 damage may lead to an abnormal morphology of the meniscus, and may indicate the necessity for surgery.

In the illustrated embodiment, a combined score $\gamma_k$ is determined using Equation 10a, Equation 10b and Equation 10c.

$$\text{if } \alpha_k > 1.5\ \beta_k \text{ then } \gamma_k = \alpha_k \quad (10a)$$

$$\text{if } \beta_k > 1.5\ \alpha_k \text{ then } \gamma_k = \beta_k \quad (10a)$$

$$\text{else } \gamma_k = (\alpha_k + \beta_k)/2 \quad (10c)$$

In other embodiments different rules are used to combine the breakability and degeneracy metrics. In some embodiments, a combined score is not determined and step 942 is omitted.

In step 950, it is determined whether the score (combined or individual) exceeds a tear threshold score. If not, then control passes to step 952 to determine a "no tear" result or decision. Control then passes to step 960, described below. If it is determined in step 950 that the score exceeds a tear threshold score, then control passes to step 954 to determine a "tear" result or decision. Control then also passes to step 960. For example, in the illustrated embodiment, it is determined during step 950 whether the combined score $\gamma_k$ is above 70 for a posterior medial meniscus object on several slices. If so control passes to step 954 to make a tear decision.

In some embodiments, a human analyst determines a tear/ no tear result based on individual or combined scores, and steps 950, 952 and 953 are omitted.

In step 960, it is determined whether there is another meniscus quadrant for which to determine tear propensity. If so, control passes back to step 910 to select the next anatomical division in the VOI, such as a posterior lateral meniscus quadrant, and determine its tear propensity. If there are no further anatomical divisions, control passes to step 270, described above to present the meniscus or its tear propensity or both to a user, such as a surgeon.

In some embodiments, only one anatomical division is considered and step 960 is omitted.

As used herein a tear propensity is any measure of the propensity of meniscus tissue to tear, whether the measure is an intensity or binary image in a meniscus object, an individual breakability or degeneracy metric, some other statistic, a metric for a single slice or weighted average among multiple adjacent slices, or a combined score, or a penultimate tear/no tear decision.

5. Presentation

Figure 12:
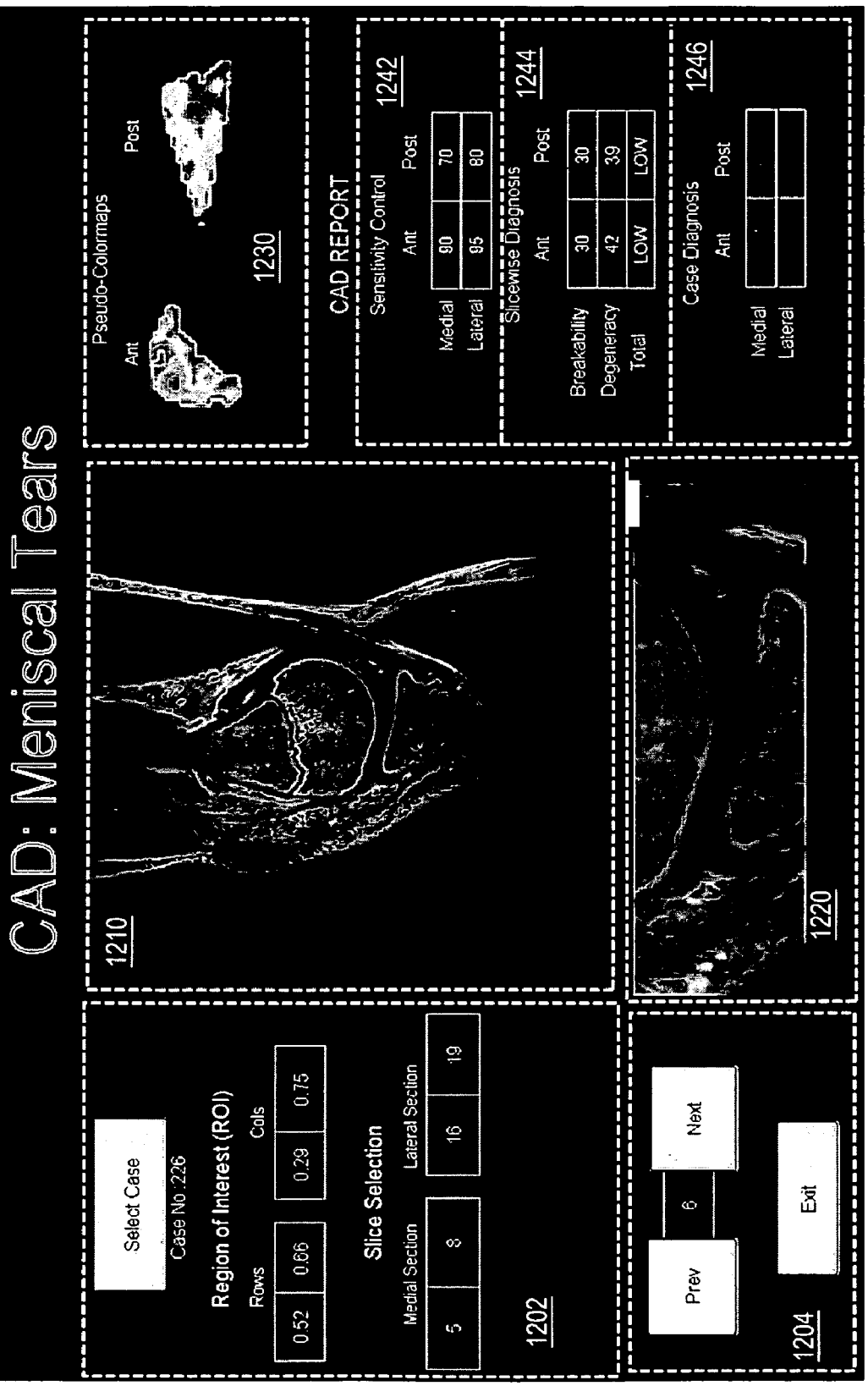
FIG. 12 is a block diagram that illustrates a presentation of results from the method of FIG. 2, according to an embodiment.

FIG. 12 is a block diagram that illustrates a Computer Aided Decision (CAD) presentation 1200 of results from the method of FIG. 2, according to an embodiment. Presentation 1200 is a particular embodiment of a presentation made during step 270 in FIG. 2. The CAD presentation 1200 format allows users to select patients' cases and run the analysis of meniscus tears. A radiologist first selects a patient's studies, runs the analysis, and then navigates through the different sagittal slices. The system displays segmentation results in real time. At the same time, it also displays the contrast-enhanced color map of the segmented meniscus, which also provides visual assessment on tear detection (analogous to the images depicted in FIG. 11A through FIG. 11D, described above). In the illustrated embodiment, the presentation display also indicates breakability and degeneracy scores and a tear/no tear decision for the case.

In the illustrated embodiment, CAD presentation 1200 includes a case selection panel 1202, a slice selection panel 1204, a slice image panel 1210, an AOI image panel 1220, a meniscus objects panel 1230, a sensitivity report panel, a slice diagnosis panel 1244, and a case diagnosis panel 1246.

The case selection panel 1202 includes display elements that indicate the case (e.g., subject and scanning device and time), the rows and columns of each slice that make up the AOI, and identifiers for the slices in the final set.

The slice selection panel 1204 includes display control elements that allow a user to navigate from one sagittal slice to another in the case, and to exit the case and CAD program.

The slice image panel 1210 includes an image display element that presents the current sagittal slice selected in panel 1204.

The AOI image panel 1220 includes an image display element that presents the scan data in the AOI only.

The meniscus objects panel 1230 includes display elements that indicate a bounding box for each meniscus like object in the AOI displayed in panel 1220. Pixels inside the bounding box but outside the convex mask are blank (indicated, for example, by a uniform blue color) as are pixels inside the convex mask but above the cartilage threshold. The remaining pixels are color coded to distinguish some or all of the Np different probe fractions of the meniscus intensity threshold. This enables a user to gain intuition about the breakability and degeneracy measures.

The sensitivity report panel includes display elements that indicate historical performance of the CAD system in detecting meniscal tears, as described in more detail in the next section.

The slice diagnosis panel 1244 includes display elements that indicate breakability and degeneracy metrics for the two objects (one anterior and one posterior) on the current slice, and gives the combined score (as low propensity for tear, moderate propensity for tear, high propensity for tear) for the meniscus objects on the current slice.

The case diagnosis panel 1246 includes display elements that indicate the tear/no tear decision (normal/tear) for the four meniscus quadrants based on all the slices in the final set.

6. Performance

The performance of the illustrated embodiment was determined in a study that was Health Insurance Portability and Accountability Act-compliant and approved by an Institutional Review Board. A pre-existing report and image repository in the inventors' institution was retrospectively searched for the keywords meniscal tear, horn, knee, and arthroscopy in individuals of all ages and both sexes who underwent MR imaging between October 2003 and July 2006. The resulting group of 910 cases was divided into those with positive and negative meniscal tear results based on MR findings. For those with positive tear findings in MR data, arthroscopic results were sought in the medical record to determine a false positive rate. All MR examinations were performed before scheduled surgery. Those with negative reports were reviewed by an experienced radiologist. Through this process, 17 cases of meniscal tears and 23 cases without meniscal tears were identified (19 males, ages 15-61 y; 21 females, ages 30-73 y). This set was used to evaluate the system 100. In addition, a group of 5 positive and 5 negative cases were identified from the 910 cases and used as training dataset in the CAD development phase to determine tear threshold scores in Table 2.

To evaluate the performance of the illustrated CAD system, 2 board-certified radiologists were asked to perform diagnosis by reading the image series for each of 40 subjects and to render diagnostic decisions on the presence or absence of tears in the 4 meniscus quadrants. Table 3 shows their detection results and the corresponding sensitivity and specificity scores. Sensitivity is true positive detections divided by a sum of true positives and false positives, as determined by a gold standard (e.g., surgical intervention). Specificity is true negative detections divided by a sum of true negatives and false positives, as determined by a gold standard.

The CAD system and the 2 radiologists were found to have the same sensitivity in detection of medial posterior tears, the most common meniscal injuries. The CAD system performed as well or slightly worse than radiologists in lateral posterior tear detection. The average sensitivities (weighted by the number of samples) of the CAD system and radiologist 1 and 2 were 83.87%, 74.19%, and 80.65%, respectively. This shows good sensitivity of the CAD system.

A significant number of negative samples were seen for each region. The average specificities (weighted by the number of samples) of the CAD system, radiologist 1, and 2 are 75.78%, 78.91%, and 85.16%. This shows good specificity of the CAD system The specificity value of CAD is within expectations because most CAD applications are designed and trained to put more cost (penalty) on missing the abnormality, a false negative, than issuing false positives.

The unsupervised meniscus extraction and tear detection demonstrated in the CAD system implements a series of custom-designed extraction and threshold techniques that are shown in a small-sample study to be closely correlated with radiologists' identification of meniscus objects and associated tears. By incorporating anatomical knowledge into the basic design of image processing techniques in this CAD system, resulting overall performance in sensitivity was close to that of radiologists. Improvements in specificity are anticipated. The development of this CAD approach shows promise for increasing radiologist productivity and confidence, improving patient outcomes, and applying more sophisticated CAD algorithms to orthopedic imaging tasks.

TABLE 3

Results of CAD system and radiologist findings for each of meniscal section

| Section | Detector | No. of detections (TP) | No. of tears | Sensitivity % | No. of rejections (TN) | No. w/o tears | Specificity % |
|---|---|---|---|---|---|---|---|
| Medial Anterior | CAD | 2 | 3 | 67 | 31 | 37 | 84 |
| | Rad1 | 2 | | 67 | 33 | | 89 |
| | Rad2 | 1 | | 33 | 34 | | 92 |
| Medial Posterior | CAD | 15 | 16 | 94 | 17 | 24 | 71 |
| | Rad1 | 15 | | 94 | 15 | | 63 |
| | Rad2 | 15 | | 94 | 20 | | 83 |
| Lateral Anterior | CAD | 3 | 4 | 75 | 25 | 36 | 70 |
| | Rad1 | 1 | | 25 | 29 | | 81 |
| | Rad2 | 2 | | 50 | 29 | | 81 |
| Lateral Posterior | CAD | 6 | 8 | 75 | 24 | 32 | 75 |
| | Rad1 | 5 | | 63 | 24 | | 75 |
| | Rad2 | 7 | | 88 | 26 | | 81 |

7. Hardware Overview

Figure 13:
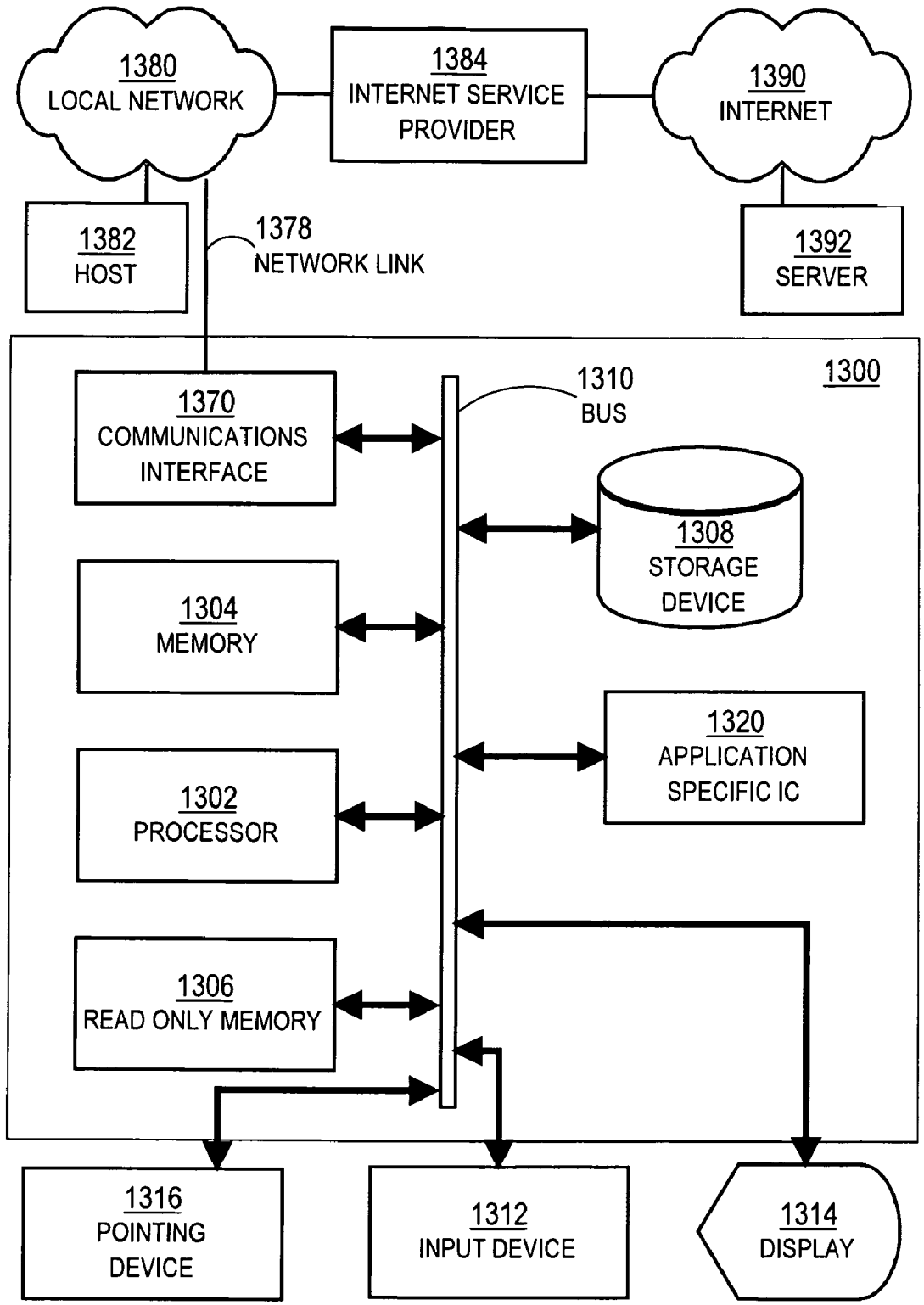
FIG. 13 is a block diagram that illustrates a computer system upon which an embodiment of the invention may be implemented.

FIG. 13 is a block diagram that illustrates a computer system 1300 upon which an embodiment of the invention may be implemented. Computer system 1300 includes a communication mechanism such as a bus 1310 for passing information between other internal and external components of the computer system 1300. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). A sequence of binary digits constitutes digital data that is used to represent a number or code for a character. A bus 1310 includes many parallel conductors of information so that information is transferred quickly among devices coupled to the bus 1310. One or more processors 1302 for processing information are coupled with the bus 1310. A processor 1302 performs a set of operations on information. The set of operations include bringing information in from the bus 1310 and placing information on the bus 1310. The set of operations also typically include comparing two or more units of information, shifting positions of units of information, and combining two or more units of information, such as by addition or multiplication. A sequence of operations to be executed by the processor 1302 constitutes computer instructions.

Computer system 1300 also includes a memory 1304 coupled to bus 1310. The memory 1304, such as a random access memory (RAM) or other dynamic storage device, stores information including computer instructions. Dynamic memory allows information stored therein to be changed by the computer system 1300. RAM allows a unit of information stored at a location called a memory address to be stored and retrieved independently of information at neighboring addresses. The memory 1304 is also used by the processor 1302 to store temporary values during execution of computer instructions. The computer system 1300 also includes a read only memory (ROM) 1306 or other static storage device coupled to the bus 1310 for storing static information, including instructions, that is not changed by the computer system 1300. Also coupled to bus 1310 is a non-volatile (persistent) storage device 1308, such as a magnetic disk or optical disk, for storing information, including instructions, that persists even when the computer system 1300 is turned off or otherwise loses power.

Information, including instructions, is provided to the bus 1310 for use by the processor from an external input device 1312, such as a keyboard containing alphanumeric keys operated by a human user, or a sensor. A sensor detects conditions in its vicinity and transforms those detections into signals compatible with the signals used to represent information in computer system 1300. Other external devices coupled to bus 1310, used primarily for interacting with humans, include a display device 1314, such as a cathode ray tube (CRT) or a liquid crystal display (LCD), for presenting images, and a pointing device 1316, such as a mouse or a trackball or cursor direction keys, for controlling a position of a small cursor image presented on the display 1314 and issuing commands associated with graphical elements presented on the display 1314.

In the illustrated embodiment, special purpose hardware, such as an application specific integrated circuit (IC) 1320, is coupled to bus 1310. The special purpose hardware is configured to perform operations not performed by processor 1302 quickly enough for special purposes. Examples of application specific ICs include graphics accelerator cards for generating images for display 1314, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1300 also includes one or more instances of a communications interface 1370 coupled to bus 1310. Communication interface 1370 provides a two-way communication coupling to a variety of external devices that operate with their own processors, such as printers, scanners and external disks. In general the coupling is with a network link 1378 that is connected to a local network 1380 to which a variety of external devices with their own processors are connected. For example, communication interface 1370 may be a parallel port or a serial port or a universal serial bus (USB) port on a personal computer. In some embodiments, communications interface 1370 is an integrated services digital network (ISDN) card or a digital subscriber line (DSL) card or a telephone modem that provides an information communication connection to a corresponding type of telephone line. In some embodiments, a communication interface 1370 is a cable modem that converts signals on bus 1310 into signals for a communication connection over a coaxial cable or into optical signals for a communication connection over a fiber optic cable. As another example, communications interface 1370 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1370 sends and receives electrical, acoustic or electromagnetic signals, including infrared and optical signals, that carry information streams, such as digital data.

The term computer-readable medium is used herein to refer to any medium that participates in providing information to processor 1302, including instructions for execution. Such a medium may take many forms, including, but not limited to, non-volatile media, volatile media and transmission media. Non-volatile media include, for example, optical or magnetic disks, such as storage device 1308. Volatile media include, for example, dynamic memory 1304. Transmission media include, for example, coaxial cables, copper wire, fiber optic cables, and waves that travel through space without wires or cables, such as acoustic waves and electromagnetic waves, including radio, optical and infrared waves.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Network link 1378 typically provides information communication through one or more networks to other devices that use or process the information. For example, network link 1378 may provide a connection through local network 1380 to a host computer 1382 or to equipment 1384 operated by an Internet Service Provider (ISP). ISP equipment 1384 in turn provides data communication services through the public, world-wide packet-switching communication network of networks now commonly referred to as the Internet 1390. A computer called a server 1392 connected to the Internet provides a service in response to information received over the Internet. For example, server 1392 provides information representing video data for presentation at display 1314.

The invention is related to the use of computer system 1300 for implementing the techniques described herein. According to one embodiment of the invention, those techniques are performed by computer system 1300 in response to processor 1302 executing one or more sequences of one or more instructions contained in memory 1304. Such instructions, also called software and program code, may be read into memory 1304 from another computer-readable medium such as storage device 1308. Execution of the sequences of instructions contained in memory 1304 causes processor 1302 to perform the method steps described herein. In alternative embodiments, hardware, such as application specific integrated circuit 1320, may be used in place of or in combination with software to implement the invention. Thus, embodiments of the invention are not limited to any specific combination of hardware and software.

The signals transmitted over network link 1378 and other networks through communications interface 1370, carry information to and from computer system 1300. Computer system 1300 can send and receive information, including program code, through the networks 1380, 1390 among others, through network link 1378 and communications interface 1370. In an example using the Internet 1390, a server 1392 transmits program code for a particular application, requested by a message sent from computer 1300, through Internet 1390, ISP equipment 1384, local network 1380 and communications interface 1370. The received code may be executed by processor 1302 as it is received, or may be stored in storage device 1308 or other non-volatile storage for later execution, or both. In this manner, computer system 1300 may obtain application program code in the form of a signal on a carrier wave.

Various forms of computer readable media may be involved in carrying one or more sequence of instructions or data or both to processor 1302 for execution. For example, instructions and data may initially be carried on a magnetic disk of a remote computer such as host 1382. The remote computer loads the instructions and data into its dynamic memory and sends the instructions and data over a telephone line using a modem. A modem local to the computer system 1300 receives the instructions and data on a telephone line and uses an infra-red transmitter to convert the instructions and data to a signal on an infra-red a carrier wave serving as the network link 1378. An infrared detector serving as communications interface 1370 receives the instructions and data carried in the infrared signal and places information representing the instructions and data onto bus 1310. Bus 1310 carries the information to memory 1304 from which processor 1302 retrieves and executes the instructions using some of the data sent with the instructions. The instructions and data received in memory 1304 may optionally be stored on storage device 1308, either before or after execution by the processor 1302.

8. Extensions and Alternatives

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for automatically detecting meniscal tears in non-invasive scans comprising:
    receiving a meniscus object portion of scan data from a scanning device;
    receiving threshold data that indicates a meniscus extraction intensity used to define the meniscus object portion of the scan data; and
    determining, without human intervention, a propensity for meniscal tears based on the threshold data and the meniscus object portion of the scan data.

2. The method as recited in claim 1, wherein receiving the meniscus object portion of the scan data further comprises determining the meniscus object portion from the scan data without human intervention.

3. The method as recited in claim 1, wherein determining the propensity for meniscal tears further comprises determining a breakability measure based on a largest breaking fraction of a plurality of fractions of the meniscus extraction threshold, wherein a threshold equal to a breaking fraction divides the meniscus object portion into a plurality of distinct portions.

4. The method as recited in claim 3, wherein determining the breakability measure further comprises determining a weighted sum of a plurality of slice breakability measures on a corresponding plurality of adjacent sagittal slices of the scan data.

5. The method as recited in claim 1, wherein determining the propensity for meniscal tears further comprises determining a degeneracy measure based on decrease in area of the meniscus object portion within a threshold equal to a fraction of the meniscus extraction threshold for a plurality of fractions.

6. The method as recited in claim 5, wherein determining the degeneracy measure further comprises determining a weighted sum of a plurality of slice degeneracy measures on a corresponding plurality of adjacent sagittal slices of the scan data.

7. The method as recited in claim 1, wherein determining the propensity for meniscal tears further comprises:
    determining if a property in the meniscus object portion of the scan data is similar to properties in historical scan data for which a tear occurred; and
    if it is determined that the property is similar, then determining that the scan data indicates a tear in a meniscus of the knee of the subject.

8. The method as recited in claim 1, wherein determining the propensity for meniscal tears further comprises, if it is determined that the property is not similar, then determining that the scan data indicates no tear in a meniscus of the knee of the subject.

9. A non-transitory computer-readable medium carrying one or more sequences of instructions for automatically determining meniscal tears in non-invasive scans, wherein execution of the one or more sequences of instructions by one or more processors causes the one or more processors to perform the steps of:
    receiving a meniscus object portion of scan data from a scanning device;
    receiving threshold data that indicates a meniscus extraction threshold used to define the meniscus object portion of the scan data; and
    determining, without human intervention, a propensity for meniscal tears based on the threshold data and the meniscus object portion of the scan data.

10. An apparatus for automatically determining meniscal tears in non-invasive scans, comprising:
    means for receiving a meniscus object portion of scan data from a scanning device;
    means for receiving threshold data that indicates a meniscus extraction threshold used to define the meniscus object portion of the scan data; and
    means for determining, without human intervention, a propensity for meniscal tears based on the threshold data and the meniscus object portion of the scan data.

* * * * *